United States Patent
Kurn et al.

(10) Patent No.: US 6,200,757 B1
(45) Date of Patent: Mar. 13, 2001

(54) METHOD FOR CONTROLLING THE EXTENSION OF AN OLIGONUCLEOTIDE

(75) Inventors: Nurith Kurn, Palo Alto; Yen Ping Liu, Cupertino; Alla Lishanski, San Jose; Marc Taylor, Mountain View, all of CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/233,413

(22) Filed: Jan. 19, 1999

(51) Int. Cl.[7] ....................................................... C12Q 1/68
(52) U.S. Cl. ........................... 435/6; 435/91.1; 435/91.2; 536/23.1; 536/24.33; 536/24.3; 536/25.3; 536/25.32; 536/26.71
(58) Field of Search ................................. 435/91.1, 91.2, 435/6; 536/23.1, 24.3, 24.33, 25.3, 25.32, 26.71

(56) References Cited

U.S. PATENT DOCUMENTS

| | | |
|---|---|---|
| 4,683,195 | 7/1987 | Mullis et al. . |
| 5,043,272 | 8/1991 | Hartley . |
| 5,338,671 | 8/1994 | Scalice et al. . |
| 5,348,853 | 9/1994 | Wang et al. . |
| 5,411,876 | 5/1995 | Bloch et al. . |
| 5,508,178 | 4/1996 | Rose et al. . |
| 5,565,339 | 10/1996 | Bloch et al. . |
| 5,599,660 | 2/1997 | Ramanujam et al. . |
| 5,705,366 | 1/1998 | Backus . |
| 5,792,607 | 8/1998 | Backman et al. . |
| 6,001,611 | * 12/1999 | Will ...................................... 435/91.2 |

FOREIGN PATENT DOCUMENTS

| | | |
|---|---|---|
| 0439182 | 1/1996 | (EP) . |
| WO 9603526A1 | 7/1995 | (WO) . |

OTHER PUBLICATIONS

Kellogg, et al., *Bio Techniques;* 16(6): 1134–1137; (1994); TaqStart Antibody™: "hot Start" PCR Facilitated by a Neutralizing Monoclonal Antibody Directed Against Taq DNA Polymerase.

(List continued on next page.)

*Primary Examiner*—Kenneth R. Horlick
*Assistant Examiner*—Janell E. Taylor
(74) *Attorney, Agent, or Firm*—Patrick G. Gattari; Theodore J Leitereg

(57) ABSTRACT

The present invention relates to a method for selectively extending an oligonucleotide primer along a specific target polynucleotide sequence in a mixture of polynucleotides. A combination is provided comprising the mixture, an oligonucleotide primer having a modification, and a binding substance for the modification wherein the binding substance binds to the oligonucleotide and prevents the extension of the oligonucleotide along the target polynucleotide sequence. The temperature of the combination is adjusted to a level sufficient to irreversibly denature the binding substance and permit the extension of the oligonucleotide primer along the specific target polynucleotide sequence. The invention has particular application in the amplification of nucleic acids. Also disclosed are kits for carrying out a method in accordance with the present invention.

28 Claims, 3 Drawing Sheets

OTHER PUBLICATIONS

Nilsson, et al., *Bio Techniques;* 22(4): 744–751; (1997); Heat–Mediated Activation of Affinity–Immobilized Taq DNA Polymerase.

Dang, et al., *J.Molecular Biol;* 264:268–278; (1996); Oligonucleotide Inhibitors of Taq DNA Polymerase Facilitate Detection of Low Copy Number Targets by PCR.

Weighardt, et al., *PCR Methods and Applications;* 3:77–80; (1993); A Simple Procedure for Enhancing PCR Specificity.

Birch, et al., *Nature;* 381: 445–446; (1996); Simplified hot start PCR.

Chou, et al., *Nucleic Acids Research;* 20(7): 1717–1723; (1992); Prevention of pre–PCR mis–priming and primer dimerization improves low–copy–number amplifications.

Barnes, *Proc. Nat. Acad. Sci. USA;* 91: 2216–2220; (1994); PCR amplification of up to 35–kb DNA with high fidelity and high yield from $\lambda$ bacteriophage templates.

Nickel, et al.; *J. Biological Chem.;* 267(2): 848–854; (1992); Interactions of Azidothymidine Triphosphate with the Celluar DNA Polymerase $\alpha, \delta$, and $\epsilon$ and with DNA Primase*.

* cited by examiner

METHOD FOR CONTROLLING THE EXTENSION OF AN OLIGONUCLEOTIDE

BACKGROUND OF THE INVENTION

1. Field of the Invention

Significant morbidity and mortality are associated with infectious diseases. More rapid and accurate diagnostic methods are required for better monitoring and treatment of disease. Molecular methods using DNA probes, nucleic acid hybridizations and in vitro amplification techniques are promising methods offering advantages to conventional methods used for patient diagnoses.

A method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The different PCR primers, which anneal to opposite strands of the DNA, are positioned so that the polymerase catalyzed extension product of one primer can serve as a template strand for the other, leading to the accumulation of a discrete fragment whose length is defined by the distance between the 5'-ends of the oligonucleotide primers.

Another method has also been described for amplifying nucleic acid sequences. This method is referred to as single primer amplification. The method provides for the amplification of a target sequence that possesses a stem-loop or inverted repeat structure where the target sequence is flanked by relatively short complementary sequences. Various methods for creating such a target sequence in relation to the presence of a polynucleotide analyte to be detected have also been described.

The amplification methods described above require that samples suspected of having a specific nucleotide sequence be heated at about 95° C. and then be repetitively thermally cycled between one or two lower temperatures and about 95° C. The higher temperatures denature duplexes and the lower temperatures permit hybridization of the primer and chain extension.

The above methods are extremely powerful techniques for high sensitivity detection of target DNA molecules present in very small amounts. The correlation between the number of original target DNA molecules and the number of specifically amplified products is influenced by a number of variables. Minor variations in buffer or temperature conditions can greatly influence reaction-to-reaction amplification efficiencies. Further, clinical samples of DNA targets can contain inhibitory factors that can suppress enzymatic amplification. In addition, such clinical samples also contain irrelevant DNA, which can be present in very large amounts relative to the target DNA molecules.

The above amplification methods suffer from interference caused by random partial hybridization of primers used in such amplification to irrelevant DNA, i.e., DNA that is not target DNA and to which the primers bind non-specifically or non-selectively. A competition between target DNA and irrelevant DNA for the enzyme and the primer thus is created. As a result the efficiency of the amplification of the target DNA molecules is decreased. At best this leads to difficulty in distinguishing amplified target DNA from amplified irrelevant DNA. The amplification of irrelevant DNA to any substantial degree can interfere with specific amplification of target DNA to prevent detection of the target DNA completely.

One approach for this problem is to avoid chain extension of low temperature non-specifically hybridized primers by heating the reaction mixture to 95° C. prior to adding a critical reagent such as a polymerase enzyme or magnesium that is required to activate the polymerase. This can be accomplished by using a wax layer to separate the various reaction components until a high temperature is reached. Alternatively, an inhibitory antibody against the polymerase can be added at low temperature. The antibody denatures at elevated temperature and allows the enzyme to become reactivated. Another approach involves the use of AmpliTaq Gold enzyme as the polymerase in PCR reactions. Another method involving chain extension of an oligonucleotide primer is a method for the detection of differences in nucleic acids described in U.S. patent application Ser. No. 08/771,623, the disclosure of which is incorporated herein by reference. Briefly, the branch migration method detects a difference between two related nucleic acid sequences. In the method, if there is a difference between the two related nucleic acid sequences, a stable quadramolecular complex is formed comprising both of the nucleic acid sequences in double stranded form. Usually, the complex comprises a Holliday junction. Both members of at least one pair of non-complementary strands within the complex have labels. The association of the labels as part of the complex is determined as an indication of the presence of the difference between the two related sequences. The method may be employed for detecting the presence of a mutation in a target nucleic acid sequence.

In the above method for the detection of differences between two related DNA sequences, non-specific priming can be a problem for mutation detection by inhibition of DNA branch migration. All amplification products incorporate the "tail" sequences of the tailed primers and hence are able to participate in the formation of four-stranded DNA complexes with both specific PCR products and with each other. Since the sequences on both sides of the junction are completely different from each other, such complexes never undergo strand separation by branch migration and thus generate non-specific signal. One approach to alleviate this problem is to use a two-step PCR procedure or nested PCR. It is highly desirable, however, to perform the above method using a single PCR reaction with just one set of primers.

A method for avoiding the above problems that is inexpensive and more controllable than the approaches mentioned above is desirable.

2. Description of the Related Art

U.S. Pat. No. 5,338,671 (Scalice, et al.) discusses DNA amplification with thermostable DNA polymerase and polymerase inhibiting antibody.

Compositions and methods for inhibiting dimerization of primers during storage of polymerase chain reaction reagents is disclosed in U.S. Pat. No. 5,565,339 (Bloch, et al.) (Bloch I).

Use of grease or wax in the polymerase chain reaction is discussed in U.S. Pat. No. 5,411,876 (Bloch, et al.) (Bloch II).

U.S. Pat. No. 5,599,660 (Ramanujam, et al.) discloses a method and preparation for sequential delivery of wax-embedded, inactivated biological and chemical reagents.

A method for reducing non-specific priming in DNA amplification is disclosed in U.S. Pat. No. 5,348,853 (Wang, et al.).

TaqStart Antibody™ used in hot start PCR facilitated by a neutralizing monoclonal antibody directed against Taq DNA polymerase is described by Kellogg, et al., *BioTechniques* (1994) 16(6): 1134–1137.

Co-amplification of target nucleic acid using volume exclusion agent in reaction composition and a test kit and test device useful therefor is discussed in U.S. Pat. No. 5,705,366 (Backus).

Heat-mediated activation of affinity-immobilized Taq DNA polymerase is described by Nilsson, et al., in *BioTechniques* (1997) 22(4):744–751.

Oligonucleotide inhibitors of Taq polymerase facilitate detection of low copy number targets by PCR are discussed by Dang, et al., *J. Mol. Biol.* (1996) 24:268–278.

A simple procedure for enhancing PCR specificity is described by Weighardt, et al., *PCR Methods and Applications* (1993) 3:77–80.

A simplified hot start PCR using AmpliTaq Gold enzyme is discussed by Birch, etal., Nature (1996) 381:445–446.

A hot start procedure using wax beads is disclosed by Chou, et al., *Nucleic Acids Research* (1992) 20:1717–1723.

W. B. Barnes discusses PCR amplification of up to 35-kb DNA with high fidelity and high yield from λ-bacteriophage templates in *Proc. Nat. Acad. Sci.* USA (1994) 91:2216–2220.

PCT application WO 96/03526A1 (Niveleau) discusses nucleic acid amplification method using a modified nucleoside and detection of the amplification product using antibodies.

Backman, et al., disclose method and kits for amplifying target nucleic acids applicable to both polymerase and ligase chain reactions in U.S. Pat. No. 5,792,607.

A process for amplifying, detecting and/or cloning nucleic acid sequences is disclosed in U.S. Patent No. 4,683,195.

U.S. Pat. No. 5,508,178 (Rose, et al.) describes nucleic acid amplification using a single polynucleotide primer. U.S. patent application Ser. No. 08/140,349 filed Oct. 20, 1993 (Laney, et al.), describes methods of introducing defined sequences at the 3'-end of polynucleotides. The disclosures of these references are incorporated herein by reference.

Amplification of nucleic acid sequences using oligonucleotides of random sequence as primers is described in U.S. Pat. No. 5,043,272 (Hartley).

Nickel, et al., *J. Biol. Chem.* (1992) 267:848–854 describes interactions of azidothymidine triphosphate with cellular DNA polymerases and with DNA primase.

EP 0 439 182 (Beckman, et al.) discusses methods of amplifying target nucleic acids applicable to both polymerase and ligase chain reactions.

SUMMARY OF THE INVENTION

In its broadest aspect the present invention relates to a method for selectively extending an oligonucleotide primer along a specific target polynucleotide sequence in a mixture of polynucleotides. A combination is provided comprising the mixture, an oligonucleotide primer having a modification, and a binding substance for the modification wherein the binding substance binds to the oligonucleotide and prevents the extension of the oligonucleotide along the target polynucleotide sequence. The temperature of the combination is adjusted sequentially or cyclically to levels sufficient to irreversibly denature the binding substance and permit the extension of the oligonucleotide primer along the specific target polynucleotide sequence.

Another aspect of the present invention is a method for controlling the extension of an oligonucleotide along a template polynucleotide. A combination is provided in a medium. The combination comprises (i) a template polynucleotide (ii) an oligonucleotide at least a portion of which hybridizes to a portion of the template polynucleotide, the oligonucleotide comprising a modified moiety, (iii) all reagents required for extending the oligonucleotide along the template polynucleotide, and (iv) a binding substance for modified moiety. The binding substance is capable of binding to the modified moiety and of preventing the oligonucleotide from extending along the template polynucleotide. The combination is subjected to conditions for releasing irreversibly the binding substance from the oligonucleotide and permitting the oligonucleotide to extend along the template polynucleotide.

Another aspect of the present invention is a method for amplifying a target polynucleotide sequence. A combination is provided comprising (i) a medium suspected of containing the target polynucleotide sequence, (ii) all reagents required for conducting an amplification of the target polynucleotide sequence, the reagents comprising a nucleotide polymerase, nucleoside triphosphates, and at least one oligonucleotide primer extendable along the target polynucleotide sequence. The oligonucleotide primer comprises a modified moiety. A binding substance for the modified moiety is included in the combination. The binding substance is capable of binding to the modified moiety and preventing the primer from being extended along the target sequence. The combination is subjected to conditions for amplifying the target polynucleotide sequence. Under such conditions, the binding substance is released irreversibly from the primer during the temperature cycling thereby permitting the primer to bind with and be extended along the target polynucleotide sequence.

Another aspect of the present invention is a method for amplifying a polynucleotide sequence of a target polynucleotide ("target sequence"). A first oligonucleotide primer ("first primer") is hybridized to the 3'-end of the target sequence. The first primer is extended, in the presence of a polymerase and nucleotide triphosphates, along at least the target sequence to produce an extended first primer. The first primer is capable of hybridizing to, and being extended along, (1) the extended first primer or (2) an extended second oligonucleotide primer ("second primer"). The extended second primer results from the extension of a second primer capable of hybridizing to and extending along a polynucleotide that is complementary (complementary polynucleotide) to the target sequence. The extended first primer is dissociated from the target sequence. The first or the second primer is hybridized to the 3'-end of the extended first primer and the first or the second primer is extended along the extended first primer. The extended first primer or the extended second primer is dissociated from the extended first primer. The first primer is hybridized to the 3'-end of the extended first or the extended second primer. The hybridization steps involving the first and/or the second primers with the extended primers are repeated by repeated temperature cycling. The primer comprises a modified nucleotide in the portion thereof that binds to the target polynucleotide. An antibody for the modified nucleotide is included in the combination. The antibody is capable of binding to the modified nucleotide and preventing the primer from extending along the target sequence. The antibody is released irreversibly from the primer during the temperature cycling thereby permitting the primer to bind with and be extended along the target polynucleotide sequence.

Another aspect of the present invention is a method for detecting a target sequence of a target polynucleotide ("target sequence"). The target sequence is subjected to a method similar to that described above. The extended first primer and/or the extended second primer are detected. The primer comprises a modified nucleotide in the portion thereof that binds to the target polynucleotide. An antibody for the modified nucleotide is included in the combination. The antibody is capable of binding to the modified nucleotide and preventing the primer from being extended along the target sequence. The antibody is released irreversibly from the primer during the temperature cycling thereby permitting the primer to bind with and be extended along the target polynucleotide sequence.

Another aspect of the present invention is a kit comprising in packaged combination (a) an oligonucleotide at least a portion of which hybridizes to a portion of a template polynucleotide, the oligonucleotide comprising a modified moiety, (b) reagents for extending the oligonucleotide along the template polynucleotide, and (c) an antibody for the modified moiety. The antibody is capable of binding to the modified moiety and preventing the oligonucleotide from extending along the template polynucleotide.

DESCRIPTION OF THE SPECIFIC EMBODIMENTS

Figure 1:
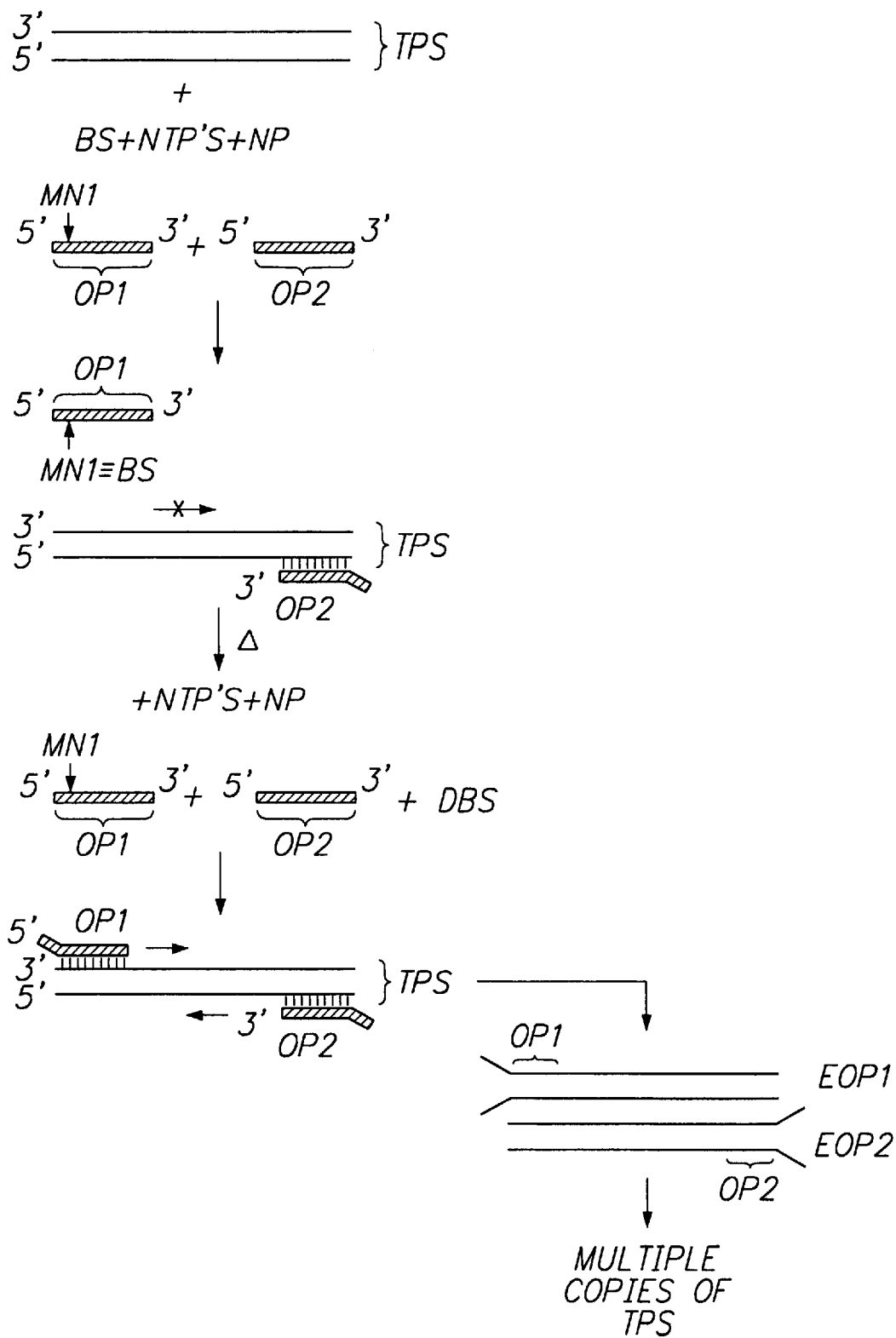
FIG. 1 is a schematic diagram depicting an embodiment in accordance with the present invention.

In the present invention premature hybridization and extension of an oligonucleotide primer is prevented by specific binding of the oligonucleotide primer by a thermally labile binding substance such as a protein. The oligonucleotide primer contains a modified moiety usually, but not necessarily, in the portion of the oligonucleotide primer that binds to a template polynucleotide. The binding substance is specific for the modified moiety and binds to the oligonucleotide primer, which prevents engagement of the polymerase and premature activation of the oligonucleotide primer and/or subsequent extension. Activation of the primer and extension of the hybridized primer are blocked by binding of the binding substance, which is thermally labile. Elevation of the temperature of the reaction medium inactivates the binding substance. The inactivation of the binding substance results in dissociation of the complex of the binding substance and the oligonucleotide primer, release of the oligonucleotide primer, formation of a specific primer-template polynucleotide hybrid, activation of the 3'-terminus of the oligonucleotide primer and extension of the primer along the template polynucleotide.

The present invention enables assembly of all reagents required for amplification in one reaction mixture, prior to onset of the amplification process. Analysis of the amplification products for the purpose of detection, sequence analysis and the like, are greatly simplified by the methods of the invention. Since the binding substance is rendered irreversibly inactive at the elevated temperature, it does not interfere in later analysis of the amplification reaction. Accordingly, the present invention results in elimination of non-specific priming at low temperatures, which is a major contributor to the production of non- specific amplification. The present method is generally independent of the polymerase used; however, in some circumstances as explained hereinbelow an exonuclease may be necessary.

The present invention provides advantages over the use of an antibody that specifically binds to single stranded DNA. Formation of single stranded species of the sample DNA during sample preparation is common. This may result in competition for binding of the DNA antibody thus resulting in premature release of active primer capable of non-specific primer extension. Another advantage of the present invention is that it is merely necessary to have a modified moiety in the oligonucleotide primer. The modified moiety may be in the portion of the oligonucleotide primer that binds to the corresponding portion of the template polynucleotide or the modified moiety may be at the 3'-terminus, the 3'-end or the 5'-end. The present method allows for assembly of amplification reaction mixtures at low temperature, thus simplifying the amplification procedure.

The method of the present invention may be used alone to achieve the above advantages. However, it is within the purview of the invention to carry out the present method in conjunction with other "hot start" procedures. For example, the present method may be used together with wax beads or with the method of U.S. patent application Ser. No. 08/965, 492.

In the present invention an amplification of a target polynucleotide sequence is conducted using an oligonucleotide having a modified moiety and a binding substance that specifically binds to such moiety. Formation of a complex between the binding substance and the oligonucleotide primer results in inhibition of the ability of the oligonucleotide primer to be extended along the template polynucleotide. When all of the amplification reagents are mixed with the sample, extension of the primer along any template polynucleotide present in the mixture is inhibited because of the presence of the complex between the binding substance and the oligonucleotide primer. As the temperature is increased, the binding substance dissociates from the complex with the primer. The oligonucleotide primer (if previously unbound) can then bind to the template ipolynucleotide sequence and undergo chain extension. The background products resulting from amplification of irrelevant DNA are greatly decreased because chain extension only takes place at an elevated temperature where binding is relatively selective.

The reaction medium is subjected to controlled conditions under which the binding substance dissociates from the complex with the oligonucleotide primer thereby releasing the oligonucleotide primer in a controlled manner for extension along the polynucleotide template.

The present method has application to a number of procedures where chain extension of an oligonucleotide along a template polynucleotide takes place. One such procedure is the amplification of a target polynucleotide sequence, e.g., an amplification carried out using thermal cycling. The use of the present method eliminates the use of nested primers or other means that were previously required to provide sufficiently low background for an amplification method to provide a meaningful result.

Before proceeding further with a description of the specific embodiments of the present invention, a number of terms will be defined.

Chain extension of an oligonucleotide—extension of an oligonucleotide along a polynucleotide template (chain of nucleotides) to produce a chain extension product that is the complement of the polynucleotide template. The polynucleotide is a template because the oligonucleotide primer is hybridizable with at least a portion of the polynucleotide and may be extended along such portion. In general, in a primer extension reaction a primer hybridizes to, and is extended along (chain extended along), at least the template sequence within a polynucleotide. The extended primers are "chain extension products." Reagents for carrying out a chain extension of an oligonucleotide primer along a polynucleotide template include a nucleotide polymerase and nucleoside triphosphates. Chain extension procedures are utilized in procedures such as amplification of polynucleotides, formation of cDNA complementary to mRNA for cloning of a given gene or a fragment thereof and so forth.

In the context of an amplification, chain extension usually involves temperature cycling, i.e., elevating the temperature of the reaction mixture to cause hybridized polynucleotide sequences to denature, cooling the reaction mixture to permit binding of an oligonucleotide primer to its respective target polynucleotide sequence and subsequent extension along the target polynucleotide sequence, and repeating the above. However, target polynucleotides may be amplified without thermocycling.

One important method utilizing chain extension of an oligonucleotide primer is that for the amplification of nucleic acids or polynucleotides, such as a target polynucleotide sequence. Such methods generally result in the formation of one or more copies of a nucleic acid or polynucleotide molecule or in the formation of one or more copies of the complement of a nucleic acid or polynucleotide molecule, usually a target polynucleotide sequence, present in a medium.

One such method for the enzymatic amplification of specific double stranded sequences of DNA is known as the polymerase chain reaction (PCR), as described above. This in vitro amplification procedure is based on repeated cycles of denaturation, annealing of at least two different oligonucleotide primers, and primer extension, i.e., "chain extension," of such primers, by thermophilic template dependent polynucleotide polymerase, resulting in the exponential increase in copies, i.e., "chain extension products of the above primers," of the target polynucleotide sequence flanked by the primers. The two different PCR primers, which anneal to opposite strands of the DNA, are positioned so that the polymerase-catalyzed extension product of one primer can serve as a template strand for the other, leading to the accumulation of a discrete double stranded fragment whose length is defined by the distance between the 5'-ends of the oligonucleotide primers.

Another method for amplification is mentioned above and involves amplification of a single stranded polynucleotide using a single polynucleotide primer. The single stranded polynucleotide that is to be amplified contains two non-contiguous sequences that are complementary to one another and, thus, are capable of hybridizing together to form a stem-loop structure. This single stranded polynucleotide may be already part of a target polynucleotide sequence or may be created as the result of the presence of a target polynucleotide sequence.

Another method involving chain extension of an oligonucleotide primer is. a method for the detection of differences in nucleic acids described in U.S. patent application Ser. No. 08/771,623, the disclosure of which is incorporated herein by reference above. Generally, in the method a medium suspected of containing two related nucleic acid sequences is treated to provide two partial duplexes each comprised of fully matched duplexes having at one end non-complementary end portions. The partial duplexes are related in that, except for the difference, one of the strands, S1, of one of the partial duplexes is complementary to one of the strands, S1, of the other of the partial duplexes and the other of the strands, S2, of one of the partial duplexes is complementary to the other of the strands, S2', of the other of the partial duplexes. The medium is subjected to conditions that permit the binding of S1 to S1 and S2 to S2', respectively. If there is a difference between the related nucleic acid sequences, a stable complex is formed comprising strands S1, S1', S2 and S2'. A determination is made whether the stable complex is formed, the presence thereof indicating the presence of a difference between the related nucleic acid sequences.

Modified moiety—a moiety that comprises a modification that distinguishes the moiety from one that does not comprise such modification.

Nucleotide—a base-sugar-phosphate combination that is, for example,—the monomeric unit of nucleic acid polymers, i.e., DNA and RNA.

Natural nucleotide—a nucleotide generally found in nature; such natural nucleotides include bases such as adenine, uridine, cytidine, thymidine, guanidine and so forth.

Non-natural nucleotide—is the unit in a modified oligonucleotide that differs from a natural nucleotide by some modification. The nature of the non-natural nucleotide for purposes of the present invention is described in more detail below in the definition of modified oligonucleotide. The non-natural nucleotide, when not bound by a binding substance, may or may not interfere to any significant degree with the ability of the modified oligonucleotide to hybridize to, and be extended along, a template polynucleotide. In the event that the non- natural nucleotide interferes with such ability, then the non-natural nucleotide should be distal from the 3'-end of the primer or should be removed from the primer prior to extension. An example of such a non-natural nucleotide is etheno-dA.

Nucleoside—is a base-sugar combination or a nucleotide lacking a phosphate moiety.

Target sequence of a target polynucleotide—a sequence of nucleotides to be identified, usually existing within a portion (target polynucleotide) or all of a polynucleotide analyte, the identity of which is known to an extent sufficient to allow preparation of various primers and other molecules necessary for conducting an amplification of the target sequence contained within the target polynucleotide. In general, in primer extension amplification primers hybridize to, and are extended along (chain extended), at least the target sequence within the target polynucleotide and, thus, the target sequence acts as a template. The extended primers are chain "extension products." The target sequence usually lies between two defined sequences, but need not. In general, the primers hybridize with the defined sequences or with at least a portion of such target polynucleotide, usually at least a ten-nucleotide segment at the 3'-end thereof and preferably at least 15, frequently 20 to 50 nucleotide segment thereof. The target sequence usually contains from about 30 to 5,000 or more nucleotides, preferably 50 to 1,000 nucleotides. The target polynucleotide is generally a fraction of a larger molecule or it may be substantially the entire molecule (polynucleotide analyte). The minimum number of nucleotides in the target polynucleotide sequence is selected to assure that the presence of target polynucleotide in a sample is a specific indicator of the presence of polynucleotide analyte in a sample. Very roughly, the sequence length is usually greater than about 1.6 log L nucleotides where L is the number of base pairs in the genome of the biologic source of the sample. The maximum number of nucleotides in the target polynucleotide is normally governed by the length of the polynucleotide analyte and its tendency to be broken by shearing or other processes during isolation and any procedures required to prepare the sample for assay and the efficiency of detection and/or amplification of the sequence.

Oligonucleotide—a single stranded polynucleotide, usually a synthetic polynucleotide. The oligonucleotide(s) are usually comprised of a sequence of about 5 to about 150 or more nucleotides, preferably, about 10 to about 100 nucleotides, more preferably, about 15 to about 50 nucleotides in length. Various well-known techniques can be employed for preparing oligonucleotides. Such sequences can be obtained by biological synthesis or by chemical synthesis. For short sequences (up to about 100 nucleotides) chemical synthesis is frequently more economical as compared to biological synthesis. For longer sequences standard replication methods employed in molecular biology can be used such as the use of M13 for single stranded DNA as described by J. Messing, *Methods Enzymol.* (1983) 101: 20–78.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

Other chemical methods of polynucleotide or oligonucleotide synthesis include phosphotriester and phosphodiester methods (Narang, et al., *Meth. Enzymol.* (1979) 68:90) and synthesis on a support (Beaucage, et al., *Tetrahedron Letters.* (1981) 22:1859–1862) as well as phosphoramidate technique, Caruthers, M. H., et al., *Methods in Enzymology* (1988)154:287–314 (1988), and others described in "Synthesis and Applications of DNA and RNA," S. A. Narang, editor, Academic Press, New York, 1987, and the references contained therein.

End of an oligonucleotide—as used herein this phrase refers to nucleotides, including the terminal nucleotide, at either the 3'- or 5' opposing sides of an oligonucleotide.

Terminus of an oligonucleotide—as used herein this term refers to the terminal nucleotide at either the 3'- or 5'- end of an oligonucleotide.

Oligonucleotide primer—an oligonucleotide that is usually employed in a chain extension on a polynucleotide template such as in, for example, an amplification of a nucleic acid. The oligonucleotide primer is usually a synthetic deoxynucleotide that is single stranded, containing a sequence at its 3'-end that is capable of hybridizing with a defined sequence of the target polynucleotide. Normally, an oligonucleotide primer, and particularly its 3'-end, has preferably at least 70%, more preferably, at least 90%, most preferably 100%, complementarily to the defined sequence. The number of nucleotides in the hybridizable sequence of an oligonucleotide primer, which hybridizes to a target polynucleotide sequence, should be such that stringency conditions used to hybridize the oligonucleotide primer will prevent excessive random non-specific hybridization. The number of nucleotides in the oligonucleotide primer will be the same as the defined sequence of the target polynucleotide to which it binds, namely, at least 12 nucleotides, preferably, at least about 15 nucleotides, and generally from about 12 to about 50 nucleotides, preferably, about 15 to about 30 nucleotides.

Modified oligonucleotide—an oligonucleotide having a modification; an oligonucleotide that possesses one or more (i) natural nucleotides that differ from the four generally recognized nucleotides and are, therefore, modified with respect to such nucleotides or (ii) non-natural nucleotides having a chemical modification (modified nucleotide) sometimes referred to herein as a "nucleotide analog") as compared to an oligonucleotide having an unmodified nucleotide. When the natural or non-natural nucleotide comprising the modification is bound by the binding substance, the oligonucleotide primer is unable to be extended along the polynucleotide to which it might hybridize. Accordingly, chain extension does not occur to any substantial degree unless and until the complex between the binding substance and the oligonucleotide primer is dissociated and the binding substance is denatured irreversibly.

The modified nucleotides for the modified oligonucleotide are selected to allow for sufficient binding to a binding substance so that the oligonucleotide is not capable of being extended along a template polynucleotide to any substantial degree. The binding substance should have a binding affinity for the modified nucleotide of at least about $10^{-8}$, usually about $10^{-9}$ to about $10^{-11}$.

The modified oligonucleotide has at least one modified nucleotide, preferably about 1 to about 3 modified nucleotides, preferably in a contiguous sequence. The modified nucleotide may be in the portion of the oligonucleotide primer that binds to the corresponding portion of the template polynucleotide or the modified nucleotide may be at the 3'-terminus, the 3'-end or the 5'-end. Where the modified nucleotide is in the portion of the oligonucleotide that binds to a target polynucleotide, the modified nucleotide should not be able to interfere with the hybridization of the oligonucleotide to a target polynucleotide. If the modified nucleotide does interfere with such hybridization, it is generally removed from the oligonucleotide prior to any extension reaction. In some embodiments, the modified nucleotide is at least 1 to 20 nucleotides, more usually, about 1 to 2 nucleotides, from the 3'-terminus. However, as explained more fully herein below, the modified nucleotide may be located near or at the 3'-terminus of the oligonucleotide and, in the event that such modified nucleotide interferes with the hybridization of the oligonucleotide with the target polynucleotide, an enzyme is added to the reaction mixture to cleave the modified nucleotide from the oligonucleotide prior to hybridization.

Any modification that accomplishes the purposes of the present invention may be utilized. The modification should be one for which a binding substance can be prepared or obtained. The modification must permit binding of the binding substance to the modified oligonucleotide.

In one embodiment the modified nucleotide is a natural nucleotide that has a 3'-hydroxyl group that has been modified such as by formation of an ester, amide, sulfate or glycoside and thus is not chain extendable. Preferably, such a modified nucleotide is heat or light labile and thus the modified nucleotide is removable as the temperature of the reaction medium is raised or the medium is irradiated, as the case may be. In another approach such a modified nucleotide may be removed enzymatically. Other methods of removal of such a modified nucleotide will be suggested to those skilled in the art in view of the above disclosure. For example, where the modification is an ester, removal is achieved in accordance with the present invention by use of an enzyme that is a thermally stable esterase. Alternatively, where a glycoside of the 3'-hydroxyl group is employed, the glycosidic linkage is cleaved by a thermally stable glycosidase. For example, a β-galactosyl group can be attached to the 3'-end of a modified oligonucleotide and a thermally stable β-galactosidase can be used in the reaction medium.

In another embodiment, the modification is selected such that the modified nucleotide or nucleotides are removed by an enzyme having 3'-exonuclease activity when the modified oligonucleotide is not bound by the binding substance or to a template polynucleotide. One factor in the selection of the modified nucleotides in this approach is the specificity of the polymerase used in an amplification. In this particular approach, the modified oligonucleotide is usually one having one or more modified nucleotides at its 3'-end. Subsequent to dissociation of the complex of the binding substance and the modified oligonucleotide, the latter is subjected to degradation by heating with an enzyme having 3' exonuclease activity. Phosphorothioates may be used to render a portion of the modified oligonucleotide resistant to degradation past the phosphorothioate group.

Chemical modifications of a natural nucleotide to produce an unnatural or modified nucleotide are described hereinbelow by way of example and not limitation. Ethenoadenosine has an ethylene bridge between the 6-amino group and the ring nitrogen at position 1 that blocks any possible hydrogen bonding. Other modifications include alkylation at the 6-oxygen of guanine, the 4-oxygen of thymine, the ring nitrogens at the 5-position of the purines, or the 3-positions of the pyrimidines, or the removal of the 2-amino group of guanine or the 4-amino group of cytosine. Heterocyclic groups other than purines and pyrimidines can also be used. In that regard it is preferable to use derivatives that can be purchased in a form convenient for solid state synthesis of the modified oligonucleotide, usually as phosphorimidates. Other heterocycles include, for example, triazine, unsubstituted pyrimidine, pyridines, deazapurines, pyridopyrroles and the like. The particular structure of the modified nucleotide is not critical so long as the enzyme can remove it when it is not hybridized and so long as it does not support chain extension.

Another suitable modification in accordance with the present invention is a natural nucleotide that is modified by incorporation of a defined moiety to the natural nucleotide. One such defined moiety is a small organic molecule. Typical examples of such small molecules that find particular application to the present method include, by way of illustration and not limitation, fluorescein, digitoxin, biotin, and the like. Such modified oligonucleotides may be prepared by methods known in the art. See, for example, "PCR Primer, A Laboratory Manual" edited by C. W. Dueksler, Cold Spring Harbor Laboratory Press (1995).

Another example, by way of illustration and not limitation, of a suitable modification is a nucleotide that is modified on the ribose. Ribonucleotides are candidates because oligonucleotides terminating in ribonucleotides cannot be extended by most polymerases. When ribonucleotides are employed, an enzyme must be included that can exolytically remove the ribonucleotide from the modified oligonucleotide when the modified oligonucleotide is not hybridized to a complementary strand and cannot readily remove the ribonucleotide when the primer is hybridized. Other examples of modification of the ribose include 3'-deoxy derivatives including those in which the 3'-hydroxy is replaced by a functionality other than hydrogen such as an azide group.

Many modified nucleotides and oligonucleotides containing such modified nucleotides are commercially available or known in the literature. For example, etheno-deoxy A, O-6-methyl deoxy G and O-4-methyl deoxy T are commercially available from Oligos Etc., Wilsonville, Oreg. Non-hydrogen bonding nucleosides are discussed by Moran, et al., in *Nucleic Acids Research* (1996) 24(11):2044–2052 and include 4-methylindole β-nucleoside, α-naphthalene nucleoside, αa-pyrene nucleoside, and the like. N3-(β-D-ribofuranoside) derivatives such as 4amino-1 -(2'-deoxy-β-D-ribofuranosyl)-2(1 H)-pyridinone and oligonucleotides comprising such modified nucleotides are disclosed by Charcruk, et al., in *Helv. Chim. Acta* (1987) 70(3):717–725. Huang, et al., discuss arabinosylcytosine 5'-triphosphate and other modified nucleosides in *Cancer Res.* (1991) 51:6110–6117. Solomon, et aL, disclose C-linked deoxyribosides of 2-hydroxypyridine and 2-hydroxyquinoline in *Tetrahedron Letters* (1991) 32(28):3297–3300; see also Solomon, et aL, *J. Org. Chem.* (1993) 58:2232–2243. Other modified nucleosides and modified oligonucleotides may be synthesized by employing well-known synthetic techniques.

The chemical modification can be introduced into the oligonucleotide to be modified by various well-known techniques as described above for the preparation of oligonucleotides in general. Either biological synthesis or chemical synthesis can be employed. In one approach phosphotriester and phosphodiester methods can be used (Narang, et al. supra) and synthesis on a support (Beaucage, et al., supra, as well as phosphoramidate technique, Caruthers, M. H., et al., supra, and others described in "Synthesis and Applications of DNA and RNA," S. A. Narang, editor, Academic Press, New York, 1987, and the references contained therein. Controlled pore glass having a modified nucleotide bound to the surface is available for solid phase DNA synthesis employing the phosphoramidate technique. Accordingly, both automated and manual synthesis can be carried out. Modified oligonucleotides containing more than one modified nucleotide can be prepared in a similar manner by adding a modified nucleotide that has a 3'-hydroxyl to which another modified nucleotide can be added and repeating this process.

In addition to standard cloning techniques, in vitro enzymatic methods may be used such as polymerase catalyzed reactions. For preparation of RNA, T7 RNA polymerase and a suitable DNA template can be used. For DNA, polymerase chain reaction (PCR) and single primer amplification are convenient.

In another approach the 3'-hydroxyl group of a natural nucleotide may be derivatized by adding a single modified nucleotide in solution phase.

Some of the references cited above disclosing modified nucleosides that can be used in the present invention also describe syntheses of oligonucleotides containing the modified nucleotides. See, for example, Solomon, et al., J. Org. Chem. (1993) 58:2232–2243 and Charczuk, et al., in Helv. Chim. Acta (1987) 70(3):717–725.

Binding substance—in the context of the present invention a binding substance is a substance that is capable of specifically binding to the modified oligonucleotide, more particularly, to the modified nucleotide(s) of the modified oligonucleotide. The binding substance is normally a protein, usually an antibody, specific binding protein, specific receptor or the like. The binding substance should be capable of being dissociated based on temperature from a complex with the modified oligonucleotide. Usually, the binding substance is irreversibly dissociated from such complex at elevated temperature, that is, a temperature at which the binding substance undergoes thermal denaturation. Preferably, the binding substance dissociates from a complex with a modified oligonucleotide at a temperature of about 45° C. to about 90° C., more preferably about 45° C. to about 60° C. Preferably, the temperature is sufficient to denature the binding substance.

Antibody—an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like and single chain analogs thereof. In addition, aggregates, polymers, and conjugates of immunoglobulins or their fragments can be used where appropriate so long as binding affinity for a particular molecule is maintained.

In general, in the preparation of a monoclonal antibody, an immunogen is injected into a mouse and, after a sufficient time, the mouse is sacrificed and spleen cells are obtained. The spleen cell chromosomes encoding desired immunoglobulins are immortalized by fusing the spleen cells with myeloma cells or with lymphoma cells, generally in the presence of polyethylene glycol. The resulting cells, which include the fused hybridomas, are allowed to grow in a selective medium, such as HAT-medium, and the surviving cells are grown in such medium using limiting dilution conditions. The cells are grown in a suitable container, e.g., microtiter wells, and the supernatant is screened for monoclonal antibodies having the desired specificity.

Various techniques exist for enhancing yields of monoclonal antibodies, such as injection of the hybridoma cells into a peritoneal cavity of a mammalian host, which accepts the cells, and harvesting the ascites fluid. Where an insufficient amount of the monoclonal antibody collects in the ascites fluid, the antibody is harvested from the blood of the host. Various conventional ways exist for isolation and purification of the monoclonal antibodies, so as to free the monoclonal antibodies from other proteins and other contaminants (see Kohler and Milstein, supra).

Phosphorothioate—a nucleotide monophosphate in which an oxygen of at least one phosphate has been replaced by sulfur. An oxygen of 1 to 5 phosphates may be replaced by sulfur, more preferably, the oxygen of 1 to 2 phosphates is replaced. These sulfur-containing modified oligonucleotides can be prepared according to known techniques. See, for example, WO9008838, WO8911486, U.S. Pat. No. 4,910, 300, EP318245, the relevant disclosures of which are incorporated herein by reference.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine(G), inosine, and derivatives and analogs thereof. The pyrimidine bases include cytosine (C), thymine (T), uracil (U), and derivatives and analogs thereof. Nucleoside triphosphates include deoxyribonucleoside triphosphates such as dATP, dCTP, dGTP and dTTP and ribonucleoside triphosphates such as rATP, rCTP, rGTP and rUTP. The term "nucleoside triphosphates" also includes derivatives and analogs thereof, which are exemplified by those derivatives that are recognized and polymerized in a similar manner to the underivatized nucleoside triphosphates. Examples of such derivatives or analogs, by way of illustration and not imitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like. The term "nucleoside triphosphate" includes the derivatives and analogs thereof.

Nucleotide polymerase—a catalyst, usually a protein enzyme, for forming an extension of an oligonucleotide along a DNA template where the extension is complementary to the template. The nucleotide polymerase is a template dependent polynucleotide polymerase and utilizes nucleoside triphosphates as building blocks for extending the 3'-end of a oligonucleotide to provide a sequence complementary with the single stranded portion of the polynucleotide to which the oligonucleotide is hybridized to form a duplex.

The nucleotide polymerases useful in the present invention must be stable under the conditions used in the present method and are usually thermally stable nucleotide polymerases. Such enzymes may be derived from any source such as cells, bacteria, such as E. coli, plants, animals, virus, thermophilic bacteria, and so forth wherein the polymerase may be modified chemically or through genetic engineering to provide for thermal stability and/or increased activity.

Usually, the catalysts are enzymes, such as DNA polymerases. Such enzymes include Pfu DNA polymerase (native and recombinant) from Stratagene, La Jolla, Calif., Ultma DNA polymerase from Perkin Elmer, Foster City, Calif., r Bst DNA polymerase from Epicentre Technologies, Madison, Wis., VENT DNA polymerase from New England Biolabs, Beverly, Mass., Tli DNA polymerase from Promega Corp., Madison, Wis., and Pwo DNA polymerase from Boehringer Mannheim, Indianapolis, Ind., and the like. See also those enzymes set forth in "PCR Primer," supra, at pages 4–5, which include Tth DNA polymerase, Tfl DNA polymerase, Tbr DNA polymerase, Hot Tub DNA polymerase, and so forth. Also included within the scope of the present invention are combinations of two or more of the above enzymes such as, for example, a combination of Taq and Pfu (100:1) and so forth.

3' to 5' exonuclease —for purposes of the present invention an enzyme is considered to be a 3' to 5' exonuclease, or to have 3' to 5'-exonuclease activity, when, under the conditions of the reactions contemplated herein, it catalyzes the removal or cleavage of nucleotides from the 3'-end of a modified oligonucleotide when such modified oligonucleotide is not hybridized to a target polynucleotide sequence and may also act as a nucleotide polymerase (in the latter sense it may be considered as a polymerase comprising a 3' to 5' exonuclease). The enzyme cleaves nucleotides of the oligonucleotide primer at least up to and including the modified nucleotides. At such point the degraded modified oligonucleotide is extendable at its 3'-terminus and can act as an oligonucleotide primer when hybridized to the target polynucleotide sequence. Some of the nucleotide polymerases mentioned above also have 3' to 5' exonuclease activity.

Polynucleotide analyte—a compound or composition to be measured in an assay; a polymeric nucleotide, which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analyses include nucleic acids from any source in purified or unpurified form including DNA (dsDNA and ssDNA), cDNA and other synthetic DNA forms, and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological materials by procedures well known in the art. Some examples of such biological materials by way of illustration and not limitation are disclosed in U.S. Pat. No. 5,508,178 (Rose, et al.), the relevant portions of which are incorporated herein by reference.

Wholly or partially sequentially—when reagents utilized in the present invention are combined other than concomitantly (simultaneously), one or more may be combined with one or more of the remaining reagents to form a subcombination. Each subcombination can then be subjected to one or more steps of the present method. Thus, each of the subcombinations can be incubated under conditions to achieve one or more of the desired results.

Hybridization (hybridizing)—in the context of nucleotide sequences these terms are used interchangeably herein. The ability of two nucleotide sequences to hybridize with each other is based on the degree of complementarily of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of co-solvents, lowering the salt concentration, and the like.

Homologous or substantially identical—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can both be DNA or one can be DNA and the other RNA.

Complementary—two sequences are complementary when the sequence of one can bind to the sequence of the other in an anti-parallel sense wherein the 3'-end of each sequence binds to the 5'-end of the other sequence and each A, T(U), G and C of one sequence is then aligned with a T(U), A, C and G. respectively, of the other sequence.

Copy of a sequence—a sequence that is a direct identical copy of a single stranded polynucleotide sequence as differentiated from a sequence that is complementary to the sequence of such single stranded polynucleotide.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-streptavidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component Cl q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, polyvinyl chloride, polyacrylamide, cross-linked dextran, agarose, polyacrylate, polyethylene, polypropylene, poly(4-methylbutene), polystyrene, polymethacrylate, polyethylene terephthalate, nylon, polyvinyl butyrate, etc.; either used by themselves or in conjunction with other materials; glass available as Bioglass, ceramics, metals, and the like. Natural or synthetic assemblies such as liposomes, phospholipid vesicles and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, J. Biol. Chem., 245:3059 (1970). The surface can have any one of a number of shapes, such as strip, rod, particle, including bead, and the like.

Label or reporter group or reporter molecule—a member of the signal producing system. Usually, the label or reporter group or molecule is conjugated to or becomes bound to a polynucleotide probe or an oligonucleotide primer and is capable of being detected directly or is detectable through a specific binding reaction that produces a detectable signal. Labels include a polynucleotide primer or specific polynucleotide sequence that can provide a template for amplification or ligation or act as a ligand such as for a repressor protein. Preferably, an oligonucleotide primer will have, or be capable of having, a label. In general, any label that is detectable can be used. The label can be isotopic or non-isotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal producing system—the signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination. The signal-producing system is described more fully in U.S. Pat. No. 5,508,178 (Rose, et al.), the relevant disclosure of which is incorporated herein by reference.

Ancillary materials—various ancillary materials will frequently be employed in the methods and assays carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

As mentioned above, in its broadest aspect the present method provides for selectively extending an oligonucleotide primer along a target polynucleotide sequence in a mixture of polynucleotides. A particular application of the method is in the amplification of nucleic acids wherein a modified oligonucleotide is employed having a portion that comprises the modification and is hybridizable to the nucleic acid. The modification may be bound by a binding substance to render the modified oligonucleotide incapable of being extended upon by the polymerase used in an amplification.

In the method an oligonucleotide primer is controllably and selectively extended along a target polynucleotide sequence in a mixture of polynucleotides. The mixture is provided in combination with a modified oligonucleotide that comprises a non-natural nucleotide and with a binding substance specific for the non-natural nucleotide. Controlled release of the modified oligonucleotide primer is achieved by adjusting the temperature of the mixture to a level sufficient to irreversibly release the binding substance from the complex with the modified oligonucleotide primer. The oligonucleotide primer is released in situ and the oligonucleotide primer selectively binds to, and is extended along, the target polynucleotide sequence. Binding of the oligonucleotide primer to irrelevant polynucleotides is substantially reduced. Accordingly, extension of oligonucleotide primer along any polynucleotides in the reaction mixture other than the target polynucleotide sequence, which usually occurs at temperatures lower than that needed for release of the primer from the complex, is avoided.

One embodiment of the present invention is depicted in FIG. 1. In this embodiment an amplification of a target polynucleotide sequence (TPS) by PCR amplification is chosen by way of example and not limitation. TPS is combined in a suitable buffered aqueous medium with modified oligonucleotide OP1 and oligonucleotide primer OP2, which are capable of hybridizing to one or the other strands of the double stranded TPS. OP1 contains modified nucleotide MN1. Also included in the reaction mixture is a proteinaceous binding substance (BS), e.g., an antibody for MN1. BS binds to MNI and prevents MO1 from being extended along TPS. Accordingly, OP1, when bound by BS, cannot be extended along TPS, nor along any irrelevant DNA to which it might hybridize. Also included in the medium are nucleoside triphosphates (NTP's) and a nucleotide polymerase NP. The temperature of the medium is relatively low, for example, being about 20° C. to 45° C. The binding substance BS becomes dissociated from OPI and denatured as the temperature of the reaction medium is increased. Accordingly, as the temperature is raised (designated by A), complexes of BS with OPI are dissociated and BS is denatured to give free oligonucleotide primer OPI and denatured binding substance DBS. As the temperature is lowered to about 50° C. to 80° C. during the next cycle and in the presence of the nucleoside triphosphates and nucleotide polymerase, OP1 hybridizes to and is extended along the strand of TPS to which it selectively hybridizes to produce extended OP1 (EOP1). At the elevated temperature binding of nucleotide sequences to one another is more selective so that OP1, which is present in a relatively low concentration, selectively binds to TPS and the amount that may be bound to irrelevant DNA is very substantially reduced. As a result background products are greatly decreased. OP2 is also extended along the strand of TPS to which it is hybridized to produce extended OP2 (EOP2). Thermal cycling results in the production of multiple copies of TPS. Control of the temperature thus results in preferential extension of OP1 along TPS due to the controlled denaturation of the complex between BS and OP1. To enhance the effect achieved in PCR through application of the present invention, OP2 is also modified and contains modified nucleotide MN2.

Figure 2:
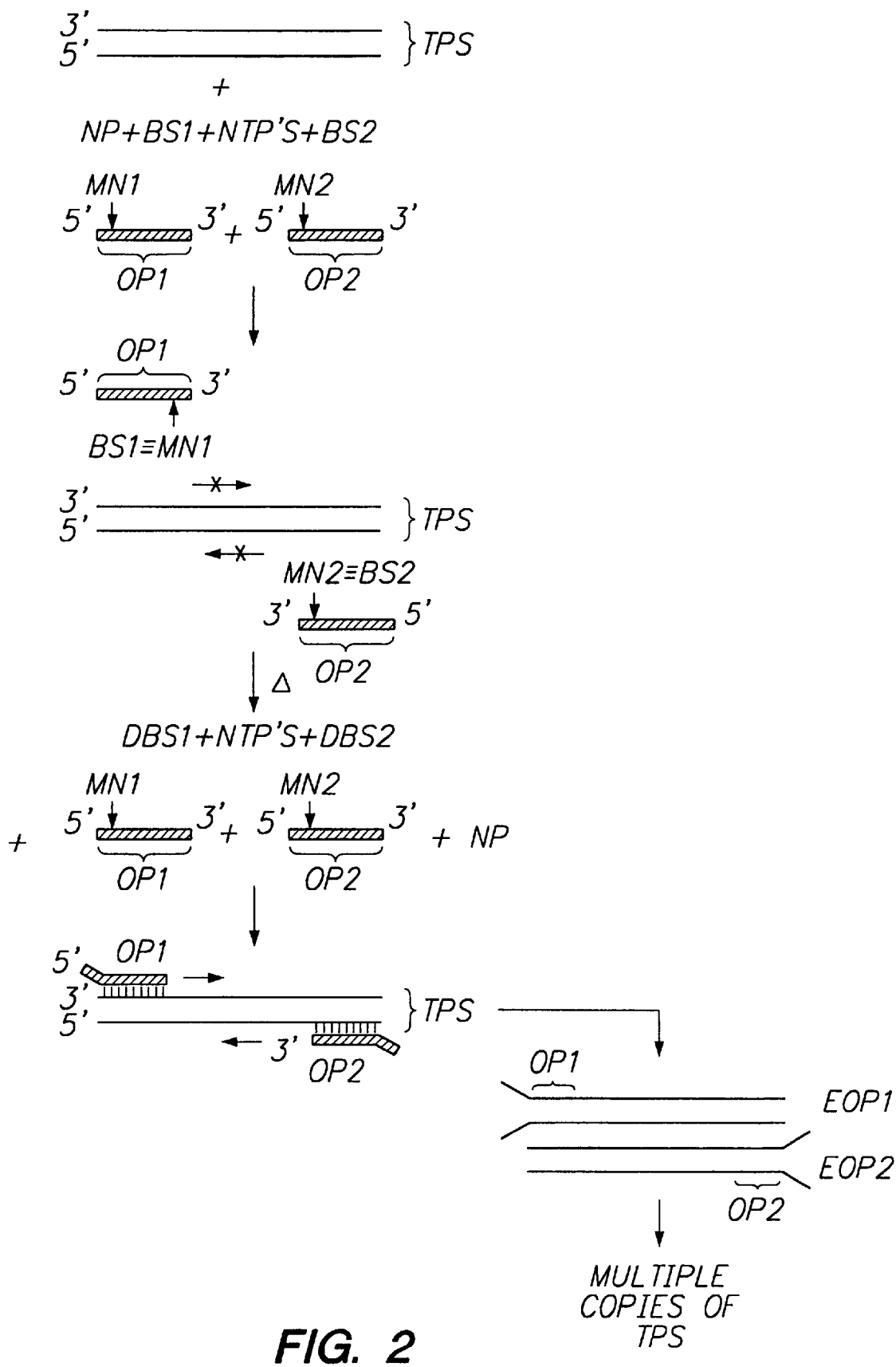
FIG. 2 is a schematic diagram depicting an alternate embodiment in accordance with the present invention.

Referring to FIG. 2, TPS is combined in a suitable buffered aqueous medium with two different oligonucleotide primers, modified oligonucleotide primer, OP1, and modified oligonucleotide primer, OP2, which are respectively capable of hybridizing to one of the strands of the double stranded TPS. Also included in the reaction medium along with binding substance, BS1, is binding substance, BS2. The binding substances may be the same or different depending on whether the modified nucleotide in OP1 is the same as or different from the modified nucleotide in OP2. BS1 binds to MN1 and prevents OP1 from being extended along TPS and BS2 binds to MN2 and prevents OP2 from being extended along TPS. Accordingly, OP1, when bound by BS1, cannot be extended along TPS, nor along any irrelevant DNA to which it might hybridize. Likewise, OP2, when bound by BS2, cannot be extended along TPS, nor along any irrelevant DNA to which it might hybridize. Also included in the medium are nucleoside triphosphates (NTP's) and a nucleotide polymerase NP. The temperature of the medium is relatively low, for example, being about 20° C. to 45° C. The binding substances, BS1 and BS2, become dissociated from OP1 and OP2, respectively, and denatured as the temperature of the reaction medium is increased. Accordingly, as the temperature is raised (designated by Δ), complexes of BS1 with OP1 and of BS2 with OP2 are dissociated and BS1 and BS2 are denatured to give free oligonucleotide primers, OP1 and OP2, and denatured binding substances, DBS1 and DBS2. As the temperature is lowered to about 50° C. to 80° C. during the next cycle and in the presence of the nucleoside triphosphates and nucleotide polymerase, OP1 is extended along the strand of TPS to which it is hybridized to produce extended OP1 (EOP1) and OP2 is also extended along the strand of TPS to which it is hybridized to produce extended OP2 (EOP2). As above in the embodiment of FIG. 1, continued thermal cycling thus leads to the production of multiple copies of TPS.

In applying the present invention to PCR amplification of nucleic acids, generally, the reaction medium is cycled between two to three temperatures. The general principle in the present invention is that extension of the oligonucleotide primer on the target polynucleotide sequence take place only at elevated temperature when binding is relatively selective. Thus, extension of the oligonucleotide primer along irrelevant polynucleotide sequences is minimized. Accordingly, the temperature of the reaction mixture is adjusted to a level sufficient to dissociate the binding substance from the modified oligonucleotide primer. In general, the temperature is raised to about 40° C. to about 100° C., preferably 50° C. to about 90° C. The time for this dissociation step is usually about 2 to about 300 seconds, more usually about 30 to about 240 seconds. Following this step, in conducting the methods, the medium is cycled between two or three temperatures. The temperatures for the methods generally range from about 10° C. to about 105° C., more usually from about 40° C. to about 99° C., preferably 50° C. to about 98° C. The exact temperatures can be varied depending on the salt concentrations, pH, solvents used, length of and composition of the target polynucleotide sequence and the primer. It is within the purview of the present invention that the dissociation step be part of an initial cycle in the amplification reaction.

Relatively low temperatures of from about 30 to about 75° C. can be employed for the extension steps, while denaturation and hybridization can be carried out at a temperature of from about 50 to about 105° C. As mentioned above the reaction medium is initially at about 20° C. to 45° C., preferably, about 25° C. to about 35° C. Relatively low temperatures of from about 50° C. to about 80° C., preferably, 50° C. to about 70° C., are employed for the hybridization or annealing steps, while denaturation is carried out at a temperature of from about 80° C. to about 100° C., preferably, 90° C. to about 95° C., and extension is carried out at a temperature of from about 70° C. to about 80° C., usually about 72° C. to about 74° C.

The amplification is conducted for a time sufficient to achieve a desired number of copies. Generally, the time period for conducting the method is from about 10 sec. to about 10 min. per cycle and any number of cycles can be used from 1 to as high as about 60 or more, usually 10 to about 50, frequently, about 20 to about 45. As a matter of convenience, it is usually desirable to minimize the time period and the number of cycles. In general, the time period for a given degree of amplification can be minimized, for example, by selecting concentrations of nucleoside triphosphates sufficient to saturate the polynucleotide polymerase, by increasing the concentrations of polynucleotide polymerase and polynucleotide primer, and by using a reaction container that provides for rapid thermal equilibration. Generally, the time period for conducting the amplification in the method of the invention is from about 5 to about 200 min. As a matter of convenience, it will usually be desirable to minimize the time period.

In carrying out the methods in accordance with the present invention, including amplification, an aqueous medium is employed. Other polar co-solvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to about 9.5, more usually in the range of about 5.5 to about 8.5, and preferably in the range of about 6 to about 8. The pH and temperature are chosen and varied, as the case may be, so as to cause, either simultaneously or sequentially, dissociation of the binding substance and the modified oligonucleotide primer and any internally hybridized sequences, hybridization of oligonucleotide primer with the target polynucleotide sequence, degradation of the 3'-end of the oligonucleotide primer hybridized to the target polynucleotide sequence, extension of the primer(s), and dissociation of the extended primer(s). In some instances, a compromise is made in optimizing the speed, efficiency and specificity of these steps depending on whether it is desired to perform the above steps sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

The concentration of the nucleotide polymerase is chosen to be sufficient to accomplish chain extension. The concentration of the polymerase is usually determined empirically. Preferably, a concentration is used that is sufficient such that further increase in the concentration does not decrease the time for the amplification by over 5-fold, preferably 2-fold. The primary limiting factor generally is the cost of the reagent.

In accordance with one aspect of the present invention, an enzyme having 3' to 5' exonuclease activity may be necessary as explained above. In this circumstance the concentration of such enzyme should be sufficient to realize the requisite level of degradation of the oligonucleotide primer containing the modified nucleotide(s) but not to achieve premature degradation of the primer. The concentration is usually about 0.1 to about 10 units per one hundred microliter reaction volume, preferably, 1 to about 5 units per one hundred microliter reaction volume.

The amount of the target polynucleotide sequence that is to be copied can be as low as one or two molecules in a sample but generally may vary from about 10 to about $10^{10}$, more usually from about 10 to about $10^8$ molecules in a sample preferably at least about $10^{-21}$ M in the sample and may be $10^{-10}$ to about $10^{-19}$ M, more usually be $10^{-14}$ to about $10^{-19}$ M.

The amount of the modified oligonucleotide is governed by the amount of oligonucleotide primer needed for the particular amplification or other reaction to which the present invention is applied. The amount of oligonucleotide primer(s) will be at least as great as the number of copies desired and will usually be about $1\times10^{-10}$ to about $1\times10^{-6}$ moles per sample, where the sample is about 1 to about 1,000 μL. Usually, the primer(s) are present in at least about 0.1 μM, preferably about 0.5 μM. Preferably, the concentration of the oligonucleotide primer(s) is substantially in excess over, preferably at least about $1 \times 10^{14}$ times greater than, the concentration of the target polynucleotide sequence.

The amount of the binding substance is governed by the amount of the modified oligonucleotide primer. Generally, the binding substance is present in at least an equivalent amount with respect to the amount of modified oligonucleotide primer and may be present in an excess over the amount of the modified oligonucleotide primer so that substantially all of the modified oligonucleotide primer is bound by the binding substance. The amount of binding substance is preferably at least 1–2 times greater than the concentration of the modified oligonucleotide primer.

The concentration of the deoxynucleoside triphosphates in the medium can vary widely; preferably, these reagents are present in an excess amount. The deoxynucleoside triphosphates are usually present at about $10^{-6}$ to about $10^{-2}$ M, preferably, about $10^{-5}$ to about $10^{-3}$ M.

The order of combining of the various reagents to form the combination may vary. Generally, the target polynucleotide is obtained from a sample containing such polynucleotide or a polynucleotide analyte that has been treated to obtain such polynucleotide. Generally, the oligonucleotide primers are combined with deoxynucleoside triphosphates and the binding substance. Next, nucleotide polymerase is added followed by the target polynucleotide. However, simultaneous addition of all of the above, as well as other step-wise or sequential orders of addition, may be employed.

The concentration and order of addition of reagents and conditions for the method are governed generally by the desire to maximize the number of copies of the extended primer(s) and the rate at which such copies are formed and the fidelity of replication. Generally, it is desirable to increase the number of copies of the extended primer by at least a factor of about $10^2$, preferably a factor of about $10^4$, more preferably, about $10^6$ or more.

In carrying out the method of the invention as applied to the detection of a polynucleotide analyte, the considerations as to media, pH, temperature and times can be as described above.

While the concentrations of the various reagents are generally determined by the concentration range of interest of the polynucleotide analyte, the final concentration of many of the reagents is normally determined empirically to optimize the sensitivity of the assay over the range of interest. The concentration of the other reagents in an assay generally is determined following the same principles as set forth above. The primary consideration is that a sufficient number of copies of extended primer(s) be produced in relation to the polynucleotide analyte sequence so that such copies can be readily detected and provide an accurate determination of the target polynucleotide sequence.

The copies of extended primer(s) can be detected in numerous ways. For example, in the present method, molecules of the oligonucleotide primer can be labeled with a reporter molecule such as a ligand, a small organic molecule, a polynucleotide sequence, a protein, support, a member of an operator-repressor pair, intercalation dye and the like. Any standard method for specifically detecting nucleic acid sequences can be used. Gel electrophoresis for detecting chain extension may be employed.

One method for detecting nucleic acids is to employ nucleic acid probes. One method utilizing probes is described in U.S. Pat. No. 4,868,104, the disclosure of which is incorporated herein by reference.

Other assay formats and detection formats are disclosed in U.S. Pat. No. 5,508,178, U.S. Pat. No. 5,439,998 and U.S. patent application Ser. No. 07/776,538 filed Oct. 11, 1991, which have been incorporated herein by reference.

Examples of particular labels or reporter molecules and their detection can be found in U.S. Pat. No. 5,439,998, the relevant disclosure of which is incorporated herein by reference.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

The present method has application where the target polynucleotide sequence is DNA or RNA.

In one aspect of the invention one or more of the reagents, such as, for example, a modified oligonucleotide and/or an oligonucleotide primer, is labeled with a label (reporter molecule). The reporter molecule can be, for example, a detectable group or a binder such as biotin or a nucleotide sequence other than the sequence that hybridizes with the target sequences. The extended primer(s) can be detected by means of a reporter molecule covalently bonded to a probe. The probe has a nucleotide sequence that is homologous or complementary to a portion of the target nucleotide sequence other than those sequences to which the primers bind.

The present invention also has application to amplification using a single oligonucleotide primer as described in U.S. Pat. No. 5,508,178 and U.S. patent application Ser. No. 08/140,349 filed Oct. 20, 1993, as well as to transcription-based amplification methods (such as, for example, NASBA or transcription mediated amplification (TMA).

The present invention also has application to a method for detecting differences in related nucleic acid sequences. The method involves chain extension of oligonucleotide primers and is described in U.S. patent application Ser. No. 08/771,623, the disclosure of which was incorporated herein by reference above. Briefly, a combination of reagents is formed in the same reaction medium and subjected to PCR. The combination comprises (i) a sample containing a target nucleic acid sequence suspected of having a mutation, (ii) a reference nucleic acid sequence, which may be added separately if it is not known to be present in the sample and which corresponds to the target nucleic acid lacking the mutation, which may be the wild type nucleic acid, (iii) a nucleotide polymerase, (iv) nucleoside triphosphates, and (v) three oligonucleotide primers where one of the primers may be labeled with different labels. As mentioned above, the medium may contain the reference nucleic acid sequence as well as the target nucleic acid sequence. Alternatively, a PCR reaction for each of the above, namely, target nucleic acid sequence and reference nucleic acid sequence, may be run separately. Thus, in the above combination of reagents, a PCR reaction mixture would contain one or the other of the target nucleic acid sequence or reference nucleic acid sequence. Subsequent to the PCR reactions for the individual sequences, the reaction mixtures are combined. In the PCR the medium is subjected to multiple temperature cycles of heating and cooling to simultaneously achieve all of the amplification reactions. Preferably, in this embodiment, each cycle includes heating the medium at about 90° C. to about 100° C. for about 2 seconds to about 3 minutes, cooling the medium to about 60° C. to about 70° C. for a period of about 5 seconds to about 3 minutes, and heating the medium at about 70° C. to about 75° C. for a period of about 10 seconds to about 3 minutes although different temperatures may be required depending on the lengths of the primer sequences. The reaction medium from above, or the combined PCR reaction mixtures if the PCR reactions are run separately, are subjected to heating for a period of time sufficient to denature double stranded molecules, preferably, at about 90° C. to about 99° C. for about 10 seconds to about 2 minutes, and cooled to about 40° C. to about 80° C., preferably about 60° C. to about 70° C., and held at this temperature for at least one minute, preferably for 20 min. to 2 hour.

Following cooling of the medium (see FIG. 3), all possible partial and complete duplexes are formed that can form from 1) single strands that have any combination of reference or mutant sequences and 5'-ends, A2 and B2, and 2) single strands having any combination of reference or mutant sequences and 5'-ends, A1 or B1 wherein the strands may further be labeled with either L1 or L2 when L1 and L2 are different. Among the partial duplexes that are formed are the tailed partial duplexes, A' and B', which can bind to each other to form complex C, which does not dissociate into duplexes D and E when a mutation is present. A determination of the presence of such a complex is then made to establish the presence of a mutation in the target nucleic acid sequence.

Figure 3:
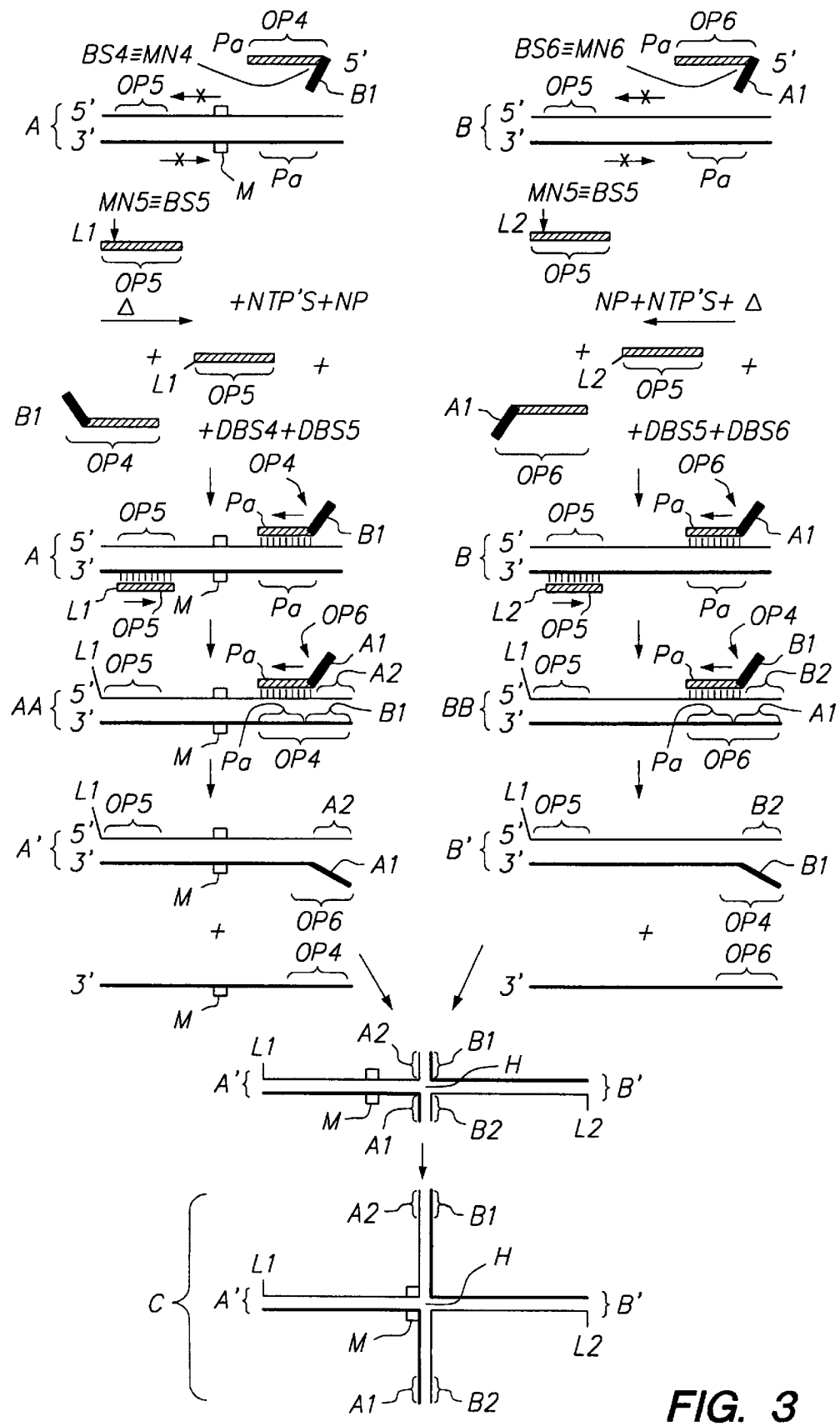
FIG. 3 is a schematic diagram depicting an alternate embodiment in accordance with the present invention.

Referring to FIG. 3, the above reactions that occur simultaneously are described in a step-wise manner. In this embodiment with application of the present invention, three modified oligonucleotides are employed and are designated OP4, OP5 and OP6, respectively. In the embodiment shown in FIG. 3, by way of illustration and not limitation, two sets of modified oligonucleotide OP5 are employed wherein one set is labeled with L1 and the other set is labeled with L2. A tailed target partial duplex A' is produced from target nucleic acid duplex A having mutation M and tailed reference partial duplex B' is produced from reference nucleic acid duplex B.

In the embodiment of FIG. 4, target nucleic acid A and reference nucleic acid B are combined in a suitable buffered aqueous medium with the modified oligonucleotides, OP4, OP5-L1 and OP5-L2, and OP6. In accordance with the present invention OP4 contains modified nucleotide MN4 and OP5-L1 contains modified nucleotide MN5. Likewise, OP6 contains modified nucleotide MN6 and OP5-L2 contains modified nucleotide MN5. The reaction medium also contains binding substances BS4, BS5 and BS6 for the respective modified nucleotides MN4, MN5 and MN6. The binding substances may be the same or different depending on whether MN4, MN5 and MN6 are the same or different. BS4 binds to MN4 and prevents OP4 from being extended along A and BS5 binds to MN5 and prevents OP5-L1 from being extended along A. Accordingly, OP4, when bound by BS4, cannot be extended along A, nor along any irrelevant DNA to which it might hybridize. Likewise, OP5-L1, when bound by BS5, cannot be extended along A, nor along any irrelevant DNA to which it might hybridize. BS6 binds to MN6 and prevents OP6 from extending along B and BS5 binds to MN5 and prevents OP5-L2 from extending along B. Accordingly, OP4, when bound by BS4, cannot be extended along B, nor along any irrelevant DNA to which it might hybridize. Likewise, OP5-L2, when bound by BS5, cannot be extended along B, nor along any irrelevant DNA to which it might hybridize. Also included in the medium are nucleoside triphosphates (NTP's) and a nucleotide polymerase, NP. The temperature of the medium is relatively low, for example, being about 20° C. to 45° C. The binding substances BS4, BS5 and BS6 become dissociated from OP4, OP5-L1, OP5-L2 and OP6, respectively, and denatured as the temperature of the reaction medium is increased. Accordingly, as the temperature is raised (designated by Δ), complexes of BS4 with OP4, of BS5 with OP5-L1 and OP5-L2 and of BS6 with OP6 are dissociated and BS4, BS5 and BS6 are denatured to give free oligonucleotide primers OP4, OP5-L1, OP5- L2 and OP6 and denatured binding substances DBS4, DBS5 and DBS6.

As the temperature is lowered to about 50° C. to about 80° C., OP4, OP5 and OP6 bind to the respective binding sites on A and B. In the presence of the nucleoside triphosphates and nucleotide polymerase, OP4, OP5 and OP6 are extended along the respective strands of A or B to which each is respectively hybridized. At the elevated temperature binding of nucleotide sequences to one another is more selective so that OP4, OP5 and OP6, which are present in a relatively low concentration, selectively bind to their respective strands of A and B so that the level at which OP4, OP5 and OP6 may be bound to irrelevant DNA is substantially reduced. Thus, consistent with the present invention, background products are greatly decreased.

As depicted in FIG. 3, A is amplified by the polymerase chain reaction using primers OP4 and OP5 to produce an amplicon AA. Primer OP5 contains a label, L1, and primer OP4 is comprised of a 3'-end portion Pa that can hybridize with the target sequence and 5'-end portion B1 that cannot hybridize with the target sequence. The amplification is carried out in the presence of a nucleotide polymerase and nucleoside triphosphates using temperature cycling. Amplicon AA has two strands, a labeled strand derived from primer OP5 and an unlabeled strand derived from primer OP4. The unlabeled strand has a 5'-end portion B1 of primer OP4 and the labeled strand has a corresponding 3'-end portion A2, which is the complement of B1. Referring again to FIG. 3, chain extension of primer OP6 along the labeled strand of amplicon AA occurs to produce tailed target partial duplex A'.

Primer OP6 is comprised of a 3'-end portion Pa, which is identical to Pa of primer OP4 and which binds to the labeled strand of AA. OP6 has 5'-end portion A1 that is not complementary to amplicon AA. In the embodiment of FIG. 3, the important strand is the complementary strand of the labeled strand and not its copy. The complementary unlabeled strand of tailed target partial duplex A' has a 5'-end portion A1, which is not complementary to the 3'-end portion A2 of the labeled strand of A'.

As mentioned above, this PCR amplification may be carried out separately as with the PCR amplification of reference nucleic acid sequence B. Alternatively, the PCR amplifications may be conducted in the presence of both target nucleic acid sequence A and reference nucleic acid sequence B.

Again referring to FIG. 3, reference nucleic acid sequence B is comprised of a sequence identical to A except for mutation M. Primer OP5 contains label L2 that is different than L1. Amplicon BB has two strands, a labeled strand derived from the extension of primer OP5-L2 and an unlabeled strand derived from the extension of primer OP6. The unlabeled strand has end portion A1 of primer OP6 and the labeled strand has corresponding end portion B2, which is the complement of A1.

Chain extension of primer OP4 along the labeled strand of amplicon BB produces tailed reference partial duplex B'. As mentioned above, primer OP4 is comprised of portion Pa, which binds to the labeled strand of BB and portion B1 that does not bind to amplicon BB. The extension product of primer OP4 has a 5'-end portion B1, which is not complementary to end portion B2 of the labeled strand of B'. As can be seen, A' and B' are related in that each of their labeled strands is complementary, except for mutation M, to the unlabeled strand of the other.

The strands of partial duplexes A' and B' bind and undergo branch migration under the reaction conditions, for example, a temperature of about 30° C. to about 75° C., preferably about 60° C. to about 70° C., for at least about 1 minute, preferably, about 15 to about 120 minutes, wherein complex C is formed. Oligonucleotide tail A1 of A' hybridizes to corresponding oligonucleotide tail B2 of B' and, similarly, oligonucleotide tail A2 of A' is hybridizes to oligonucleotide tail B1 of B'.

Branch migration within complex C continues under the above temperature conditions with separation of the complex into duplexes D and E unless a mutation M is present, whereupon branch migration and strand dissociation is inhibited. Complex C is then detected, the presence of which is directly related to the presence of mutation M.

In the embodiment depicted in FIG. 3, labels L1 and L2 are incorporated into the partial duplexes that comprise complex C and provide a means for detection of complex C. This is by way of illustration and not limitation and other convenient methods for detecting complex C may be employed, such as the use of a receptor for the complex. In this approach there is required only one label, L1 or L2, which comprises an sbp member or a reporter molecule. A receptor for the sbp member and a receptor that can bind to complex C by virtue of a feature other than L1 or L2 can both bind to complex C and provide a means for detection.

The conditions for carrying out the detection of differences in nucleic acids wherein the present invention is utilized are similar to those for the amplification described above. In general, the medium is heated to a temperature of about 90° C. to about 100° C. for a period of about 2 to about 500 seconds and then cooled to about 20° C. to about 80° C. for a period of about 5 to about 2000 seconds followed by heating to about 40° C. to about 80° C. for a period of about 5 to about 2000 seconds. Preferably, the medium is subjected to heating at about 90° C. to about 100° C. for a period of about 10 seconds to about 3 minute, cooling to about 50° C. to about 65° C. for a period of about 10 seconds to about 2 minute and heating to about 70° C. to about 80° C. for a period of about 30 seconds to about 5 minutes.

As a matter of convenience, predetermined amounts of reagents employed in the present invention can be provided in a kit in packaged combination. A kit can comprise in packaged combination one or more modified oligonucleotide primers, one or more binding substances for the modified oligonucleotide primers, nucleotide triphosphates and a nucleotide polymerase. In one embodiment the nucleotide analog is a natural nucleotide having a chemical modification. In the event that a nucleotide polymerase is included in the kit and the nucleotide polymerase does not have 3' to 5'exonuclease activity, then the kit further comprises an enzyme having 3'to 5'exonuclease activity only where it is important to remove one or more modified nucleotides at the 3'-end of the modified oligonucleotide primer.

A kit for amplification of a target polynucleotide sequence comprises the above items and, for conducting PCR, includes two oligonucleotide primers, both of which are modified. The oligonucleotide primers are related in that a product of the extension of one along said target sequence serves as a template for the extension of the other.

In assaying for a polynucleotide analyte in a sample, a kit useful in the present method can comprise, in packaged combination with other reagents mentioned above, reagents for forming a target polynucleotide sequence from a polynucleotide analyte. Furthermore, an oligonucleotide primer can be labeled or can be provided with groups to render the sequence labeled or bound to a support. The kit can further include a labeled polynucleotide probe capable of binding to an amplified target polynucleotide sequence. The kit can further include members of a signal producing system and also various buffered media, some of which may contain one or more of the above reagents.

The relative amounts of the various reagents in the kits can be varied widely to provide for concentrations of the reagents, which substantially optimize the reactions that need to occur during the present method and to further substantially optimize the sensitivity of the assay.

Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kit can further include a written description of a method in accordance with the present invention as described above.

EXAMPLES

The invention is demonstrated further by the following illustrative examples. Temperatures are in degrees Centigrade (° C.) and parts and percentages are by weight, unless otherwise indicated.

The following definitions and abbreviations are used herein:

Tris HCl—Tris(hydroxymethyl)aminomethane-HCl (a 1 M stock solution) from BioWhittaker, Walkersville, Md.

DTT—1,4-dithiothreitol from Sigma Chemical Company, St. Louis, Mo.

HPLC—high performance liquid chromatography.

DPP—4,7-diphenylphenanthroline from Aldrich Chemical Company, Milwaukee Wis.

BSA—bovine serum albumin from Sigma Chemical Company, St. Louis Mo.

ELISA—enzyme linked immunosorbent assay as described in "Enzyme-Immunoassay," Edward T. Maggio, CRC Press, Inc., Boca Raton, Fla. (1980)

bp—base pairs wt (WT)—wild type ddc—dideoxycytidine g—grams mmol—millimoles nmol—nanomoles mM—millimolar
nM—nanomolar
DMF—dimethyl formamide
THF—tetrahydrofuran
LSIMS—liquid matrix secondary ion mass spectrometry
NMR—nuclear magnetic resonance spectrometry
TMSCl—tetramethylsilylchloride
EDAC—1-ethyl-3-(3-dimethylaminopropyl)-carbodiimide hydrochloride.
MES—2-(N-morpholino)ethane sulfonic acid.
SPDP—N-succinimidyl 3-(2-pyridylthio)-propionate.
sulfo—SMCC - sulfosuccinimidyl - 4-(N-maleimidomethyl)cyclohexane-1-carboxylate.
TCEP—tris-carboxyethyl phosphine.
Sav—streptavidin
dd—double distilled
MOPS—3-(N-morpholino)propanesulfonic acid
SATA—N-succinimidyl S-acetylthioacetate
EDTA—ethylenediaminetetraacetic acid
R.B.—round bottom
RLU—relative light units Preparation of Reagents Beads:

Acc-Ab$_{Dig}$- Acceptor beads coupled (MAD) to the anti-Dig antibody (with 377 antibody molecules per bead) were prepared as follows:

Hydroxypropylaminodextran (1NH$_2$/7 glucose) was prepared by dissolving Dextran T-500 (Pharmacia, Uppsala, Sweden) (50 g) in 150 mL of H$_2$O in a 3-neck round-bottom flask equipped with mechanical stirrer and dropping funnel. To the above solution was added 18.8 g of Zn(BF$_4$)$_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran (1NH$_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 10 mL of this solution was added 23.1 mg of Sulfo-SMCC in 1 mL of water. This mixture was incubated for 1 hr at room temperature and used without further purification.

C-28 thioxene was prepared as follows:

To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with CH$_2$Cl$_2$ (400 mL). The CH$_2$Cl$_2$ solution was washed with 1 N aqueous NaOH (2x), H$_2$O, and brine, was dried over Na$_2$SO$_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-(C$_{14}$H$_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at -300° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3x). The combined organic phases were washed with H$_2$O (2x), then brine and were dried over MgSO$_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (MS (C$_{42}$H$_{69}$NO$_2$): [M—H]$^+$618.6, $^1$H NMR (250 MHz, CDCl$_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCl (50 mL, 394 mmol); and the reaction solution was heated at reflux for another 3 hr. The resulting solution was cooled, was made basic with cold 2.5 N aqueous NaOH and was extracted with CH$_2$Cl$_2$ (3x). The combined organic layers were washed with saturated aqueous NaHCO$_3$ (2x) and brine, was dried over Na$_2$SO$_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as an orange-yellow oil (MS (C$_{44}$H$_{71}$NOS): [M—H]$^+$661.6, $^1$H NMR (250 MHz, CDCl$_3$) was consistent with the expected C-28 thioxene product 2-(4-(N,N-di-(C$_{14}$H$_{29}$)-anilino)-3-phenyl thioxene.

Carboxyl chemiluminiscer (acceptor) beads (TAR beads): The following dye composition was employed; 20% C-28 thioxene (prepared as described above), 1.6% 1-chloro-9,10-bis(phenylethynyl)anthracene (1-Cl-BPEA) (from Aldrich Chemical Company) and 2.7% rubrene (from (from Aldrich Chemical Company). The particles were latex particles (Seradyn Particle Technology, Indianapolis Ind.). The dye composition (240–250 MM C-28 thioxene, 8–16 MM 1-Cl-BPEA, and 20–30 MM rubrene) was incorporated into the latex beads in a manner similar to that described in U.S. Pat. No. 5,340,716 issued Aug. 23,1994 (the '716 patent), at column 48, lines 24–45, which is incorporated herein by reference. The dyeing process involved the addition of the latex beads (10% solids) into a mixture of ethylene glycol (65.4%), 2-ethoxyethanol (32.2%) and 0.1 N NaOH (2.3%). The beads were mixed and heated for 40 min. at 95° C. with continuous stirring. While the beads are being heated, the three chemiluminescent dyes were dissolved in 2-ethoxyethanol by heating them to 95° C. for 30 min. with continuous stirring. At the end of both incubations, the dye solution was poured into the bead suspension and the resulting mixture was incubated for an additional 20 min. with continuous stirring. Following the 20-minute incubation, the beads were removed form the oil bath and are allowed to cool to 40° C.±10° C. The beads were then passed through a 43-micron mesh polyester filter and washed. The dyed particles were washed using a Microgon (Microgon Inc., Laguna Hills, Calif.). The beads were first washed with a solvent mixture composed of ethylene glycol and 2-ethoxyethanol (70%/30%). The beads were washed with 500 ml of solvent mixture per gram of beads. This is followed by a 10 % aqueous ethanol (pH 10–11) wash. The wash volume was 400 mL per gram of beads. The beads were then collected and tested for % solid, dye content, particle size, signal and background generation.

Carboxyl acceptor beads prepared above (99 mg in 4.5 mL water) were added slowly with vortexing to 5.5 mL of MAD aminodextran from above, followed by 1 mL of 200 mg/mL NHS in 50 mM MES, pH 6,1 mL of 200 mg/mL EDAC in water, and 450 µL of 1 M HCl, final pH 6. The mixture was incubated overnight at room temperature in the dark, then reacted with 200 mg succinic anhydride in 0.5 mL of DMSO for 30 min at room temperature. Freshly opened Surfact-Amps Tween-20 (Pierce Chemical Company, Rockford, Ill.) was added and the beads were centrifuged 30 min at 15,000 rpm in a Sorvall RC-5B centrifuge, washed by centrifugation with three 10mL portions of 50 mM MOPS, 50 mM EDTA, 0.1% Surfact-Amps Tween-20 (Pierce Chemical Company), pH 7.2, and resuspended in 3 mL of the same.

Monoclonal anti-digoxin Ab (prepared as described above) was purified by ABx resin (Baker Chemical Company, Phillipsburg, N.J.) and was dialyzed into 0.15 M NaCl, 5 mM $Na_2HPO_4$, pH 7.4. The anti-digoxin Ab was thiolated by mixing 622 µL (4.28 mg) with 10.2 µL of SATA (1.25 mg/mL in ethanol, 2 eq.), incubating for 1 hr at room temperature and dialyzing cold against 2×2 L of 150 mM NaCl, 10 mM $Na_2HPO_{4,}$ 1 mM EDTA, pH7. The thioacetylated antibody was deacetylated by adding 62.2 µL of hydroxylamine (1 M $H_2NOH$, 50 mM MOPS, 25 mM EDTA, pH 7), bubbling with argon and incubating for 1 hr at room temperature. The product was applied to a Pharmacia PD-10 column (G-25) and eluted with 50 mM MOPS, 50 mM EDTA, pH 7.2, bubbled with argon. After 2.5 mL fore-run, three-1 mL fractions were collected and combined. Recovery of antibody was 3.66 mg or 86% by $A_{280}$. Surfact-Amps Tween-20 (10%) was added to give 0.2% final concentration.

A 1.4 mL aliquot of the thiolated antibody above (1.71 mg antibody) was immediately added to 300 µL (10 mg) of maleimidated beads prepared above plus enough 10% Tween-20 to bring final concentration of the mixture to 0.2%. The tube was purged with argon and incubated overnight at room temperature in the dark. To the above was added 3.4 µL of 1 M $HSCH_2COOH$ in water. After 30 min at room temperature, 6.8 µL of $ICH_2COOH$ (1 M in water) was added. After 30 min 3.5 mL of 0.17 M glycine, 0.1 M NaCl, 0.1% (v/v) Tween-20, 10 mg/mL BSA, pH 9.2 was added and the beads were centrifuged (30 min at 15,000 rpm), incubated for 3 hr in 5 mL of the same buffer, centrifuged, washed by centrifugation with three-5 mL portions of Buffer C, resuspended in 5 mL of Buffer C and stored under refrigeration. The size of the beads, determined in Buffer C, was 301+/-56 nm. Binding capacity was determined with $^{125}I$-digoxin and was equivalent to 377 antibody molecules per bead.

Silicon tetra-t-butyl phthalocyanine was prepared as follows:

Sodium metal, freshly cut (5.0 g, 208 mmol), was added to 300 mL of anhydrous ether in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCl Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued. During the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (18 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask and concentrated sulfuric acid (500 mL) was added with stirring. The mixture was stirred for 4 hr. at 60° C. and was then carefully diluted with crushed ice (2000 g). The resulting mixture was filtered and the solid wad washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a silica gel column (hexane) to give 10g of pure product di-(tri-n-hexylsilyl)-silicon tetra-t-butyl phthalocyanine as a dark blue solid. (MS: $[M-H]^+$ 1364.2, absorption spectra: methanol: 674nm ($\epsilon$180,000): toluene 678nm, $^1H$ NMR (250 MHz, $CDCl_3$):δ-2.4(m,12H), -1.3(m, 12H), 0.2–0.9 (m, 54H), 1.8(s, 36H), 8.3(d, 4H) and 9.6 (m, 8H) was consistent with the above expected product.

Sens-SAv—Sensitizer beads coupled to Streptavidin (2300 SAv/bead). The sensitizer beads were prepared placing 600 mL of carboxylate modified beads (Seradyn) in a three-necked, round-bottom flask equipped with a mechanical stirrer, a glass stopper with a thermometer attached to it in one neck, and a funnel in the opposite neck. The flask had been immersed in an oil bath maintained at 94+/−1° C. The beads were added to the flask through the funnel in the neck and the bead container was rinsed with 830 mL of ethoxyethanol, 1700 mL of ethylene glycol and 60 mL of 0.1 N NaOH and the rinse was added to the flask through the funnel. The funnel was replaced with a 24–40 rubber septum. The beads were stirred at 765 rpm at a temperature of 94+/−1° C. for 40 min.

Silicon tetra4-butyl phthalocyanine (10.0 g) was dissolved in 300 mL of benzyl alcohol at 60+/−50° C. and 85 mL was added to the above round bottom flask through the septum by means of a syringe heated to 120+/−10° C. at a rate of 3 mL per min. The remaining 85 mL of the phthalocyanine solution was then added as described above. The syringe and flask originally containing the phthalocyanine was rinsed with 40 mL of benzyl alcohol and transferred to round-bottom flask. After 15 min 900 mL of deionized water and 75 mL of 0.1 N NaOH was added dropwise over 40 min. The temperature of the oil bath was allowed to drop slowly to 40+/−10° C. and stirring was then discontinued. The beads were then filtered through a 43 micron polyester filter and subjected to a Microgon tangential flow filtration apparatus (Microgon Inc., Laguna Hills, Calif.) using ethanol:water, 100:0 to 10:90, and then filtered through a 43 micron polyester filter.

Sulfo-SMCC (11.55 mg) was dissolved in 0.5 mL distilled water. Slowly, during 10 sec, the above solution was added to 5 mL of stirring aminodextran (Molecular Probes, Eugene, Oreg.) solution (12.5 mg/mL in 50 mM MOPS, pH 7.2). The mixture was incubated for 1 hr at room temperature.

To the stirring solution above was added 5 mL of 20 mg/mL (100 mg) of the sensitizer beads prepared above in distilled water. Then, 1 mL of 200 mg/mL NHS (prepared fresh in 50 mM MES, pH adjusted to 6.0 with 6 N NaOH). 200 mg EDAC was dissolved in 1 mL distilled water and this solution was added slowly with stirring to the sensitizer beads. The pH was adjusted to 6.0 by addition of 450μL of 1 N HCl and the mixture was incubated overnight in the dark. A solution of 100mg of succinic anhydride in 0.5mL of DMSO was added to the sensitizer beads and the mixture was incubated for 30 min at room temperature in the dark. To this mixture was added 0.13mL 10% Tween-20 bringing the final concentration of Tween-20 to 0.1 %. The beads were centrifuged for 45 min at 15,000 rpm as above. The supernatant was discarded and the beads were resuspended in 10 mL of buffer (50 mM MOPS, 50 mM EDTA and 0.1 % Tween-20, pH 7.2). The mixture was sonicated to disperse the beads. The beads were centrifuged for 30 min as described above, the supernatant was discarded and the beads were resuspended. This procedure was repeated for a total of three times. Then, the beads were resuspended to 40 mg/mL in 2.5 mL of the above buffer, saturated with argon and Tween-20 was added to a concentration of 0.1 %. The beads were stored at 4° C.

Streptavidin was bound to the above beads using 25 mg streptavidin for 100 mg of beads. 25 mg streptavidin (50 mg Aaston solid from Aaston, Wellesley, Mass.) was dissolved in 1 mL of 1 mM EDTA, pH 7.5, and 77 μL of 2.5 mg/mL SATA in ethanol was added thereto. The mixture was incubated for 30 min at room temperature. A deacetylation solution was prepared containing 1 M hydroxylamine-HCl, 50 mM $Na_2PO_4$, 25 mM EDTA, pH 7.0. 0.1 mL of this deacetylation solution was added to the above solution and incubated for 1 hr at room temperature. The resulting thiolated streptavidin was purified on a Pharmacia PD1 0 column and washed with a column buffer containing 50 mM MOPS, 50 mM EDTA, pH 7.2. The volume of the sample was brought to 2.5 mL by adding 1.5 mL of the above column buffer. The sample was loaded on the column and eluted with 3.5 mL of the column buffer. The thiolated streptavidin was diluted to 5 mL by adding 1.5 mL of 50 mM MOPS, 50 mM EDTA, 0.1% Tween-20, pH 7.2. 5 mL of the thiolated streptavidin solution was added to 5 mL of the sensitizer beads, under argon, and mixed well. The beads were topped with argon for 1 min, the tube was sealed and the reaction mixture was incubated overnight at room temperature in the dark.

To the above beads was added 7.5 mL of 50 mM MOPS, 50 mM EDTA, 0.1% Tween-20, pH 7.2 to bring the beads to 1 mg/mL. The remaining maleimides were capped by adding mercaptoacetic acid at a final concentration of 2 mM. The mixture was incubated in the dark for 30 min at room temperature. The remaining thiols were capped by adding iodoacetic acid at a final concentration of 10 mM and the mixture was incubated at room temperature for 30 min in the dark. The beads were centrifuged for 30 min at 15,000 rpm as above for a total of three times.

Example 1

Detection of polymorphic site in exon 11 of human BRCAL gene:

The amplification of a 450 bp long sequence of exon 11 of the BRCA1 lo gene for conducting the method of the '623 patent application was carried out in two steps. The first PCR amplification was carried out using two 5'tailed primers. The primers were composed of a 3'part, which is complementary to the target gene sequence, and a 5'part (underlined below) composed of a sequence that is not related to the target gene sequence. The two primers were modified at the 3'-end by the substitution of a fluorescein modified dT for the natural nucleotide, as shown. The primers were from Oligos, Etc.

Following initial PCR amplification, a second amplification was carried out with primers designed for the method of the '623 patent application. The forward primers were composed of a sequence that was complementary to the sequence of the 5'-tail of the first round forward primer, and were 5'-labeled with either biotin or digoxigenin (Dig). The reverse primers were composed of a 3'sequence complementary to the 5'- tail of the first PCR reverse primer, and a 5'-tail composed of a sequence that was not complementary to the target gene or the first round PCR primers. The 5'-tails of the two reverse primers were not related to each other and were designed for the formation of amplification products capable of formation of four stranded DNA structures which are used for the detection of sequence alteration by the method of the '623 application.

The sequences of the primers were as follows:
First PCR forward primer:
5'-GTTTTCCCAGTCACGACGAGGCTTTEMGTA TCCATNG-3'(SEQ ID NO:1)
First PCR reverse primer:
5'-AGGAAACAGCTATGACCATCAAAACCTAG ACCTCCTTNG-3'(SEQ ID NO:2)

The underlined portion in the above sequences represents the "tail" sequences; the non-underlined portion is complementary to the target DNA; the N denotes C6 dT fluorescein Second PCR forward primer:
5'-biotin-GTTTTCCCAGTCACGACG-3'(SEQ ID NO:3)
5'-DIG.- GTTTTCCCAGTCACGACG-3'(SEQ ID NO:4)

Second PCR reverse primers:
5'-ACCATGCTCGAGATTACGAGAGGAAACAG CTATGACCAT-3'(SEQ ID NO:5)
5'-GATCCTAGGCCTCACGTATTAGGAAACAGC TATGACCAT-3'(SEQ ID NO:6)

The underlined portion in each of the above sequences represents the "tail" sequences; the non-underlined portion is complementary to the amplification product of the first PCR reaction.

The PCR amplification with hot start using PCR wax gems was set up as follows: Aliquots of 25 µl of a partial reaction mixture containing 10 mM Tris-HCl buffer, pH 8.3, 50 mM KCl, 1.5 mM $MgCl_2$, 0.2 mg/ml BSA, 0.25 mM of each dNTP, and 0.5 µM of each of the primers was placed into PCR tubes containing a PCR gem (from Perkin-Elmer; Cat. # N-808-0150). The tubes were incubated at 85° C. for 2 min. to melt the wax and cooled to room temperature to form the wax barrier. 20 µl of a second reaction mixture containing 10 mM Tris-HCl pH 8.3, 50 mM KCl, 1,5 mM $MgCl_2$, and 5 units of Pfu DNA polymerase (Stratagene; Cat. # 600159-81 or Taq DNA polymerase (Stratagene, La Jolla, Calif.) was added to each tube. 5 µl sample, which may contain a target nucleic acid, was added to the tubes, and the reaction tubes were subjected to thermal cycling (Trio thermoblock, Biometra Inc., Tampa, Fla., Cat. # 050090005).

Reactions carried out using the method of the present invention were set up as follows: 5 µl sample was added to a reaction mixture containing the following: 10 mM Tris-HCl, pH 8.3,50 mM KCl, 1.5 mM $MgCl_2$, 0.2 mg/ml BSA, 0.25 mM of each dNTP, 0.5 µM of each primer, 2.5 units of Pfu polymerase or Taq DNA polymerase, with or without 12.5 µM anti-fluorescein monoclonal antibody (prepared by known methods similar to that described above for anti-digoxin antibody).

The reaction mixtures (total volume 25 µl) were subjected to thermal cycling as above. Thermocycling for the first PCR amplification reaction was as follows: 4 min. at 94° C.; 35 cycles of 30 sec at 94° C., 1 min. at 64° C. and 1 min. at 72° C.

An aliquot of the reaction mixture of the first amplification reaction was used for the second amplification reaction. Thermocycling for the second PCR amplification was carried out as follows: 4 min. at 94° C., followed by 20 cycles of 30 seconds at 94° C., 1 min. at 64° C. and 1 min. at 72° C.

Two genomic DNA samples (Myriad Genetics, Salt Lake City, Utah) were used in the analysis: Genomic DNA purified from cells, which are heterozygous for the polymorphic site and cells, which are homozygous. The method of the '623 patent application was carried out in this example without the addition of reference DNA amplification product since the DNA samples were from diploid cells, and the aim of the analysis was to examine homozygosity or heterozygosity of the sequence tested.

Following amplification, 2 µl of test amplification reaction mixture was mixed with 4 µl of buffer. The mixture was subjected to the following incubation conditions: 2 min. at 95° C. for denaturation of the amplification products, followed by 30 min. incubation at 65° C. for annealing, formation of the four stranded DNA structures and branch migration. 50 µl of a particle mixture (2.5 µg of sensitizer particles with immobilized streptavidin and 1.25 µg of chemiluminescer particles with immobilized anti-digoxin antibody) was added to each reaction tube. The tubes were transferred to a reader for reading the signal, incubated at 37° C. for 30 min., and signal was read (3 cycles of 1 sec. illumination and 1 sec. read). The results are summarized in Tables 1 and 2.

TABLE 1

Amplification products generated with Pfu DNA polymerase:

| | Signal Reading (RLU) | | |
|---|---|---|---|
| DNA Sample | With Wax Gems[1] | With Antibody[2] | Without Antibody[3] |
| Heterozygous | 591296 | 872780 | 1630000 |
| Homozygous | 60692 | 69318 | 868996 |
| None | 7618 | 10084 | 16840 |

[1]Known method
[2]Method in accordance with the present invention
[3]Control

TABLE 2

Amplification products generated with Taq DNA polymerase:

| | Signal Reading (RLU) | | |
|---|---|---|---|
| DNA Sample | With Wax Gems[1] | With Antibody[2] | Without Antibody[3] |
| Heterozygous | 89626 | 134662 | 346000 |
| Homozygous | 22602 | 18958 | 273350 |
| None | 5758 | 7238 | 14022 |

[1]Known method
[2]Method in accordance with the present invention
[3]Control

The above results demonstrate that antibody (anti-fluorescein antibody in this example) binding to the primers prior to amplification results in marked reduction of non-specific amplification, either target-dependent or target-independent. The method of the '623 patent application is a very sensitive method for the detection of the formation of non-specific amplification products, since branch migration cannot take place when four-stranded DNA structures are formed by non-specific products. The examples further demonstrate that the method in accordance with the present invention is not limited to a particular thermostable DNA polymerase.

Example 2

Exon 10 of the human cystic fibrosis gene

Eight samples of human genomic DNA (four wild type homozygotes and four heterozygotes with one wild type allele and one allele carrying a 3-bp deletion, Δ508) were amplified using the following primers to generate a product 220 bp in length. The genomic DNA samples were from Mayo Foundation (Rochester, Minn.).

The forward primer sequence:
5'-CTCAGTTTTCCTGGATTATGCCNNA-3'(SEQ ID NO:7)
where N=etheno-dA An equimolar mixture (125 nM each) of the 5'-biotinylated and 5'-digoxigenin labeled forward primers was used in PCR.

The sequence of the first reverse primer:
5'-ACCATGCTCGAGATTACGAGCTMCCGATTGA ATATGGAGCCNNG-3'(SEQ ID NO:8)

The sequence of the second reverse primer:
5'-GATCCTAGGCCTCACGTATTCTAACCGATTGMT ATGGAGCCNNG-3'(SEQ ID NO:9)

In the above the "tail" sequences are underlined; N=etheno-dA.

An equimolar mixture (125 nM each) of the two reverse primers was used in PCR. The 20 µl PCR reaction mixtures contained 200 µM each dNTP, 10 ng genomic DNA and 1 U of Pfu DNA polymerase. The buffer contained 10 mM Tris-HCl (pH 8.3), 50 mM KCl, 4mM MgCl$_2$ and 200 µg/ml BSA (buffer A). Two sets of PCR reactions were assembled at room temperature. One of the sets contained the anti-etheno monoclonal antibody (from Dr. P. Lorenz, Germany) at 250 nM. Pfu polymerase was the last component added to the reaction mixtures. The reactions were pre-incubated at room temperature for 30 min. before starting the thermocycling. A total of 40 cycles in the Biometra Trio thermocycler were performed consisting of a 30 sec. denaturation step at 94° C., a 1 min reannealing step at 64° C. and a 1 min. extension step at 72° C., preceded by a 4 min. denaturation of genomic DNA at 95° C.

Immediately after PCR amplification, the entire reactions were subjected to branch migration. The branch migration protocol consisted of a 2 min. denaturation step at 94° C. followed by a 30 min. reannealing/strand exchange step at 65° C.

A 2 µl aliquot of each branch migration reaction was combined with 50 µl of buffer A containing 2.5 µl (5 µg) Sensitizer-Streptavidin beads and 1.25 µl (2.5 µg) of Chemiluminescer-Anti-Dig Antibody beads and incubated for 30 min. at 37° C. The signal was then read using a signal reader. The results are summarized in Table 3.

TABLE 3

| | Signal Reading (RLU) | |
|---|---|---|
| Sample | No Anti-Etheno Antibody[1] | With Anti-Etheno Antibody[2] |
| wt/wt | 9626 | 7896 |
| wt/wt | 7240 | 8588 |
| wt/wt | 7984 | 7496 |
| wt/wt | 7972 | 7116 |
| ΔF508/wt | 262268 | 374424 |
| ΔF508/wt | 258164 | 374000 |
| ΔF508/wt | 100208 | 385916 |
| ΔF508/wt | 169350 | 384366 |

[1]Control
[2]Method in accordance with the present invention

The presence of the anti-etheno antibody resulted in higher and more uniform positive signals. This effect is presumably due to the decrease in the amount of non-specific PCR products that normally compete with the desired amplicon for enzyme and primers.

Example 3

Exon 11 of the human cystic fibrosis gene

Sixteen samples of human genomic DNA (six (6) wild type homozygotes, eight (8) heterozygotes with one wild type allele and one allele carrying G542X, G551 D, R553X or R560T point mutation and two double mutants) were amplified using the following primers to generate a product 333 bp in length. The genomic DNA samples were from Mayo Foundation (Rochester, Minn.).

The forward primer sequence:
5'-GCCTTTCAAATTCAGATTGAGCNNA-3'(SEQ ID NO:10)
where N=etheno-dA An equimolar mixture (125 nM each) of the 5'-biotinylated and 5'-digoxigenin labeled forward primers was used in PCR.

The sequence of the first reverse primer:
5'-ACCATGCTCGAGATTACGAGGACATTTACAGC AAATGCTTGCNNA-3'(SEQ ID NO:11)

The sequence of the second reverse primer:
5'-GATCCTAGGCCTCACGTATTGACATTTACAG CAAATGCTTGCNNA-3'(SEQ ID NO:9)

In the above the "tail" sequences are underlined and N=etheno-dA.

All experimental conditions were exactly the same as described in Example 2 for exon 10. The results are summarized in Table 4.

TABLE 4

| | Signal Reading (RLU) | |
|---|---|---|
| Sample | No Anti-Etheno Antibody[1] | With Anti-Etheno Antibody[2] |
| wt/wt | 6430 | 4130 |
| wt/wt | 5208 | 4380 |
| wt/wt | 6436 | 4656 |
| wt/wt | 7282 | 4486 |
| wt/wt | 7258 | 5488 |
| wt/wt | 8406 | 5442 |
| G542X/wt | 37588 | 85638 |
| G542X/wt | 60706 | 101896 |
| G551D/wt | 23340 | 85816 |
| G551D/wt | 31388 | 153038 |
| R553X/wt | 13660 | 81996 |
| R553X/wt | 20978 | 99774 |
| R560T/wt | 30374 | 129776 |
| R560T/wt | 42100 | 128442 |
| G551D/R553X | 38908 | 151542 |
| G551D/R553X | 35964 | 166728 |

[1]Control
[2]Method in accordance with the present invention

When the anti-etheno antibody is present, a significant increase in signal for the heterozygotes was again observed. The background signal for the wild type samples was somewhat lower.

Example 4

Comparison of Modified Forward and Reverse Primers with Modified Forward Primer and Unmodified Reverse Primer The following two experiments demonstrated that the advantages of the present invention were achieved when all the branch migration primers were modified and are capable of binding to the corresponding antibody that was employed. In the following example both forward and reverse "branch migration" PCR primers were modified and thus were capable of binding the antibody. An improvement in priming specificity was obtained.

The experimental conditions for amplification of exon 10 of the human cystic fibrosis gene were exactly the same as described above in Example 2. Seven genomic DNA samples included three (3) wild type homozygotes, three (3) ΔF508 and one ΔI507 heterozygote (both mutations are 3-bp deletions). The anti-etheno monoclonal antibody was present in all the reaction mixtures.

Table 5 summarizes the experiment in which two sets of PCR primers were compared: in one of the sets (left column) both forward and reverse primers were 3'-etheno modified as shown in Example 2, and in another set (right column) only the forward labeled primers were 3'-etheno modified and the reverse tailed primers were not modified (no NNA at their 3'-ends).

TABLE 5

| | Signal Reading (RLU) | |
|---|---|---|
| sample | forward primers: 3'-etheno reverse primers: 3'-etheno | forward primers: 3'-etheno reverse primers: no 3'-etheno |
| wt/wt | 3494 | 29464 |
| wt/wt | 4488 | 91644 |
| wt/wt | 3944 | 69822 |
| ΔF508/wt | 679646 | 1030254 |
| ΔF508/wt | 625680 | 971278 |
| ΔF508/wt | 617978 | 1043210 |
| ΔI507/wt | 579500 | 998724 |

The above experiment demonstrates that the method of the present invention achieves better results with the use of modified forward and reverse primers as compared to the use of a modified forward primer and an unmodified reverse primer.

Example 5

Method of the Present Invention Compared to Known Methods

The use of a method in accordance with the present invention in conjunction with the method of the '623 application patent was performed using the etheno-modified primer set Ex11 -f2e/r1e in the presence or absence of anti-ethenoadenine monoclonal antibody (MAb), both without wax gems. In addition, two other controls were conducted, in which the corresponding non-etheno primer set, Ex 1 -f2/r1, was used with either no hot-start method or with wax gems. The f2/r1 primer set flanks 173 bases of the CFTR Exon 11 sequence, resulting in an amplicon which includes 217 bases from Exon 11 and 20 bases from the reverse primer tails for a total of 237 bp.

The Exi11 -f2e/r1e primers used were as follows:

Forward primers (etheno modified):
5'-biotin-TAGAAGGMGATGTGCCTTTCANNA (SEQ ID NO:12)
5'-digoxigenin-TAGMGGMGATGTGCCTTTCANNA (SEQ ID NO: 13)
   where N etheno dA Reverse primers (etheno modified):
5'-GATCCTAGGCCTCACGTATTGACATTTACAGCAAATGCTTGCNNA-3'(SEQ ID NO:9)
5'-ACCATGCTCGAGATTACGAGGACATTTACAGCAAATGCTTGCNNA-3'(SEQ ID NO:11)
   where N=etheno dA Non-etheno primers were the same except that they lacked NNA-3'ends.

One WT & one (mixed) Heterozygote (R553D/ΔF508) were assayed in triplicate using each of the five conditions (i.e., Non-Etheno/No Wax, Etheno/No Wax and Etheno/MAb Hot-Start, Non-Etheno/Wax, & Etheno/Wax). In addition, a water blank and a heterozygous positive control (G551 DANT) were included in each reaction set.

Preparation of reagents:

| 10X Buffer D: | 100 mM Tris.HCl pH 8.3 at RT 500 mM KCl, 40 mM MgCl$_2$, 2 mg/ml BSA |
|---|---|
| 1X dNTP mixture: | 2.5 mM each of ATP, CTP, GTP, & TTP in ddH$_2$O |
| 1X Primer Sets: | 6.25 μM forward primer mixture/ 6.25 μM reverse primer mixture in ddH$_2$O |
| Target DNA: | 10 ng/μl in 1X-TE Buffer 1X-TE Buffer = 10 mM Tris.HCl pH 7.4, 1 mM Na$_2$EDTA |

Reaction Protocol

Below is a tabulation of the reagent volumes for preparing the Control Mixture (NM=No Hot-Start) and the MAb Mixture (MM=Added MAb) solutions for 2 strips of reaction tubes (8 tubes/strip). The Pfu DNA polymerase was added last. The water, buffer, nucleotides, and primers with or without MAb* were mixed and incubated at RT for 10 min. During this incubation, the bottom (BL) and top (TL, without Pfu polymerase) layers for the Wax Gem Mixture (WM=Wax Gem Hot-Start) were also prepared. When the incubation was complete, Pfu polymerase was added to each mixture (i.e., NM, MM, & the TL of the WM) immediately prior to distribution to each appropriate strip tube.

*MAb & Primer in a 1:1 volume ratio (i.e., 8.4 pmoles MAb/20 pl tube, -0.42 pM MAb) resulted in a 1:2 ratio of antibody combining sites with primer termini containing ethenoadenine dimers. That is, one equivalent volume of MAb corresponded to a 50% titration of all ethenoadenine-containing primers.

| Layer | Reagent | Volume | Comments |
|---|---|---|---|
| | No Hot-Start Mix: | | |
| (NM) | ddH$_2$O | 112.6 μl | |
| (2 sets) | 10X Buffer D | 16.8 μl | |
| | 1X ΣdNTP's | 13.44 μl | |
| | Σprimers | 6.72 μl | Exon 11-Set D (f2/r1) or Exon 11-Set D-etheno (f2e/r1e) |
| | Pfu DNA Polymerase | 1.68 μl | |
| | | 151.2 μl | (18 μl per tube) + 2 μl DNA |
| or | | | |
| | MAb Hot-Start Mix: | | |
| (MM) | ddH$_2$O | 105.8 μl | |
| (1 set) | 10X Buffer D | 16.8 μl | |
| | 1X ΣdNTP's | 13.44 μl | |
| | Σprimers | 6.72 μl | Exon 11-Set D-etheno (f2e/r1e) |
| | Anti-etheno MAb | 6.72 μl | 12.5 μM MAb |
| Upon incubation for 10 min. at RT, the following was added: | | | |
| | Pfu DNA Polymerase | 1.68 μl | |
| | | 151.2 μl | (18 μl per tube) + 2 μl DNA |
| or | | | |
| | Wax Gem Hot-Start Mix (bottom layer): | | |
| (WM-BL) | ddH$_2$O | 106.92 μl | BioWhittaker (#16-001Y) |
| (2 sets) | 10X Buffer D | 16.2 μl | |
| | 1X ΣdNTP's | 25.92 μl | Pharmacia (#27-2035-02) |
| | Σprimers | 12.96 μl | Exon 11-Set D (f2/r1) or Exon 11-Set De (f2e/r1e) |
| | | 129.6 μl | (18 μl BL per tube) |
| | Wax Layer: | | Perkin-Elmer Ampliwax PCR Gems |

-continued

| Layer | Reagent | Volume | Comments |
|---|---|---|---|
| Wax Gem Hot-Start Mix (top layer): | | | |
| (WM-TL) | ddH$_2$O | 110.16 µl | |
| (2 sets) | 10X Buffer D | 16.2 µl | |
| | Pfu DNA Polymerase | 3.24 µl | |
| | | 180.0 µl | (14.4 µl TL per tube) + 3.6 µl DNA |

Aliquots of 18 µl WM-BL were added to each tube of one of the three strips. One wax gem was transferred to each tube of this strip. The strips were sealed and placed into a thermocycler. The wax beads were melted by incubation at 85° C. for 2 min. and the wax barrier was formed by subsequent cooling to room temperature. 14.4 µl WM-TL was added to each corresponding tube in the WM strip. Test DNA sample (see below for details), 3.6 µl, was added into the tubes of this strip and stirred gently to mix.

Test DNA sample, 2 µl (see below for details), was added into one tube of each strip. An aliquot of 18 µl NM or MM was added to each tube of these two strips (avoid bubbles), stirring gently to mix.

DNA Test Samples:

| Tube # | DNA I.D. # | Genotype | Comments | Expected Result |
|---|---|---|---|---|
| 1. | C1./IMR91 | WT/WT | WT | − |
| 2. | C1./IMR91 | WT/WT | WT | − |
| 3. | C1./IMR91 | WT/WT | WT | − |
| 4. | Blank | H$_2$O AL 100797 | Neg. Control | − |
| 5. | C4./07552 | R553X/ΔF508 | Ex10&11 Mutant | + |
| 6. | C4./07552 | R553X/ΔF508 | Ex10&11 Mutant | + |
| 7. | C4./07552 | R553X/ΔF508 | Ex10&11 Mutant | + |
| 8. | C3./08338 | G551D/WT | Ex11 Mutant | + |

The method of the '623 patent application was performed in a Biometra trio thermocycler using the following sequence: 4 min at 95° C.; then, 40 cycles of 30 sec at 94° C., 1 min at 64° C. and 1 min at 72° C.; then, 2 min at 95° C. to denature the amplified products, followed by 30 min at 65° C. to allow re-annealing, formation of the four-stranded structures and branch migration.

A 2 µl aliquot of each branch migration reaction was combined with 50 µl of buffer A (see Example 2) containing 2.33 µg of Sensitizer-Sav beads and 1.16 µg of Chemiluminescer-Anti-Dig Antibody beads and incubated for 30 min at 37° C. The signal was then read using a signal reader (3 cycles of 1 sec illumination with a 1 sec read.

The cystic fibrosis exon 11 results are summarized in Table 6.

TABLE 6

| Tube # | DNA I.D. # | Genotype | Signal Counts (RLU) | Expected Result | Observed Result |
|---|---|---|---|---|---|
| Non-etheno/No Wax | | | | | |
| 1. | C1./IMR91 | WT/WT | 63026 | − | FP |
| 2. | C1./IMR91 | WT/WT | 34164 | − | FP |
| 3. | C1./IMR91 | WT/WT | 38302 | − | FP |
| 4. | Blank | H$_2$O AL 100797 | 9214 | − | − |
| 5. | C4./07552 | R553X/ΔF508 | 65254 | + | + |

TABLE 6-continued

| Tube # | DNA I.D. # | Genotype | Signal Counts (RLU) | Expected Result | Observed Result |
|---|---|---|---|---|---|
| 6. | C4./07552 | R553X/ΔF508 | 75200 | + | + |
| 7. | C4./07552 | R553X/ΔF508 | 97054 | + | + |
| 8. | C3./08338 | G551D/WT | 72384 | + | + |
| Etheno/No Wax | | | | | |
| 1. | C1./IMR91 | WT/WT | 5850 | − | − |
| 2. | C1./IMR91 | WT/WT | 6774 | − | − |
| 3. | C1./IMR91 | WT/WT | 6068 | − | − |
| 4. | Blank | H$_2$O AL 100797 | 8404 | − | − |
| 5. | C4./07552 | R553X/ΔF508 | 108688 | + | + |
| 6. | C4./07552 | R553X/ΔF508 | 88624 | + | + |
| 7. | C4./07552 | R553X/ΔF508 | 95486 | + | + |
| 8. | C3./08338 | G551D/WT | 102846 | + | + |
| Etheno/MAb | | | | | |
| 1. | C1./IMR91 | WT/WT | 4968 | − | − |
| 2. | C1./IMR91 | WT/WT | 5138 | − | − |
| 3. | C1./IMR91 | WT/WT | 5340 | − | − |
| 4. | Blank | H$_2$O AL 100797 | 7682 | − | − |
| 5. | C4./07552 | R553X/ΔF508 | 338170 | + | ++ |
| 6. | C4./07552 | R553X/ΔF508 | 317508 | + | ++ |
| 7. | C4./07552 | R553X/ΔF508 | 321056 | + | ++ |
| 8. | C3./08338 | G551D/WT | 289190 | + | ++ |
| Non-ethenol Wax | | | | | |
| 1. | C1./IMR91 | WT/WT | 13588 | − | −/HB |
| 2. | C1./IMR91 | WT/WT | 20320 | − | −/HB |
| 3. | C1./IMR91 | WT/WT | 13012 | − | −/HB |
| 4. | Blank | H$_2$O AL 100797 | 10014 | − | −/HB |
| 5. | C4./07552 | R553X/ΔF508 | 170658 | + | + |
| 6. | C4./07552 | R553X/ΔF508 | 167804 | + | + |
| 7. | C4./07552 | R553X/ΔF508 | 192894 | + | + |
| 8. | C3./08338 | G551D/WT | 172868 | + | + |
| Ethenol Wax | | | | | |
| 1. | C1./IMR91 | WT/WT | 5094 | − | − |
| 2. | C1./IMR91 | WT/WT | 7754 | − | − |
| 3. | C1./IMR91 | WT/WT | 5078 | − | − |
| 4. | Blank | H$_2$O AL 100797 | 6104 | − | − |
| 5. | C4./07552 | R553X/ΔF508 | 340588 | + | ++ |
| 6. | C4./07552 | R553X/ΔF508 | 350484 | + | ++ |
| 7. | C4./07552 | R553X/ΔF508 | 400650 | + | ++ |
| 8. | C3./08338 | G551D/WT | 356344 | + | ++ |

Abbreviations:
− Negative
+ Positive
FP False Positive
FN False Negative
HB High Background

TABLE 7

Tabulation of the average values for the triplicate sample results shown above in Table 6

| Reaction I.D. | Background Signal (RLU) | Positive Signal (RLU) | Signal/Background Ratio (unitless value) |
|---|---|---|---|
| NonEtheno/No Wax | 45164 ± 15607 | 79169 ± 16267 | 1.75 ± 0.70 |
| Etheno/No Wax | 6231 ± 483 | 97599 ± 10198 | 15.66 ± 2.04 |
| Etheno/MAb | 5149 ± 186 | 325578 ± 11048 | 63.24 ± 3.14 |
| NonEtheno/Wax | 15640 ± 4063 | 177119 ± 13736 | 11.32 ± 3.07 |
| Etheno/Wax | 5975 ± 1540 | 363907 ± 32203 | 60.90 ± 16.60 |

Conclusions

When no hot start method was employed, there was no significant discrimination between wild type and positive samples (S/B=1.8±0.7). Use of either etheno-modified primers or wax gems alone resulted in moderate levels of discrimination (S/B=15.7±2.0 or 11.3±3.1, respectively) due to both significant drops in the negative sample background levels and to small increases in the positive sample signals. The combination of etheno-modified primers with either wax gems or monoclonal antibody gave further significant increases in positive sample signals, resulting in quite respectable S/B ratios (60.9±16.6 or 63.2±3.1). The use of etheno-modified primers with MAb gave both the highest S/B ratio and the lowest CV (5.0 %, compared to 13 to 40 % for the remaining four methods).

In summary, use of anti-etheno dA monoclonal antibody resulted in low background, high positive sample signals, and high S/B ratio with low associated error, which are at least as good as those observed with etheno-modified primers with wax gems in the absence of monoclonal antibody. In addition, use of etheno-modified primers with monoclonal antibody proved to be a more convenient method of hot start than the use of wax gems in terms of reduced labor, lower necessary reaction volume, and greater ease of amplicon recovery.

All publications and patent applications cited in this specification are herein incorporated by reference as if each individual publication or patent application were specifically and individually indicated to be incorporated by reference. A portion of the present disclosure contains material that may be subject to copyright protection. The copyright owner has no objection to the facsimile reproduction by anyone of the patent document or the patent disclosure as it appears in the U.S. Patent and Trademark Office patent files or records, but otherwise reserves all copyright rights whatsoever.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for selectively extending an oligonucleotide primer along a target polynucleotide sequence in a mixture of polynucleotides, said method comprising:
    (a) providing in combination said mixture, an oligonucleotide primer having a modification, and a binding substance for said modification wherein said binding substance binds to said oligonucleotide and prevents the extension of said oligonucleotide along said target polynucleotide sequence and
    (b) adjusting the temperature of said combination to a level sufficient to irreversibly denature said binding substance and permit the extension of said oligonucleotide primer along said specific target polynucleotide sequence.

2. A method for controlling the extension of an oligonucleotide along a template polynucleotide, said method comprising:
    (a) providing in combination in a medium (i) a template polynucleotide (ii) an oligonucleotide at least a portion of which hybridizes to a portion of said template polynucleotide, said oligonucleotide comprising a modified moiety, (iii) all reagents required for extending said oligonucleotide along said template polynucleotide, and (iv) a binding substance for said modified moiety, said binding substance being capable of binding to said modified moiety and preventing said oligonucleotide from extending along said template polynucleotide, and
    (b) subjecting said combination to conditions for releasing irreversibly said binding substance from said oligonucleotide and permitting said oligonucleotide to extend along said template polynucleotide.

3. A method according to claim 2 wherein said modified moiety is a modified nucleotide.

4. A method according to claim 3 wherein said modified nucleotide is an unnatural nucleotide or comprises a group that is unnatural.

5. A method according to claim 2 wherein said template polynucleotide is DNA or RNA.

6. A method according to claim 2 that is part of an amplification method.

7. A method according to claim 6 wherein said amplification method is selected from the group consisting of polymerase chain reaction, single primer amplification, and transcription-based nucleic acid amplification.

8. A method according to claim 2 wherein said binding substance is a protein.

9. A method according to claim 2 wherein said binding substance is an antibody.

10. A method for amplifying a target polynucleotide sequence, which comprises:
    (a) providing in combination (i) a medium suspected of containing said target polynucleotide sequence, (ii) all reagents required for conducting an amplification of said target polynucleotide sequence, said reagents comprising a nucleotide polymerase, nucleoside triphosphates, and at least one primer extendable along said target polynucleotide sequence, and
    (b) subjecting said combination to conditions for amplifying said target polynucleotide sequence,
    wherein said primer comprises a modified moiety and wherein a binding substance for said modified moiety is included in said combination, said binding substance being capable of binding to said modified moiety and preventing said oligonucleotide from extending along said target polynucleotide sequence and wherein said binding substance is released irreversibly from said primer during said temperature cycling thereby permitting said primer to bind with and be extended along said target polynucleotide sequence.

11. A method according to claim 10 wherein said modified moiety is a modified nucleotide.

12. A method according to claim 11 wherein said modified nucleotide is an unnatural nucleotide or comprises a group that is unnatural.

13. A method according to claim 10 wherein said target polynucleotide is DNA or RNA.

14. A method according to claim 10 wherein only one primer is used and said target sequence contains at its 5'-end at least a 10-base sequence hybridizable with a sequence at the 3'-end of said target sequence to which said primer hybridizes.

15. A method according to claim 10 wherein first and second primers are employed and extended first primer is a template for said second primer and extended second primer is a template for said first primer.

16. A method according to claim 10 wherein said binding substance is a protein.

17. A method according to claim 10 wherein said binding substance is an antibody.

18. A method for amplifying a polynucleotide sequence of a target polynucleotide ("target sequence"), said method comprising:

(a) hybridizing to the 3'-end of said target sequence a first oligonucleotide primer ("first primer"), (b) extending, in the presence of a polymerase and nucleotide triphosphates, said first primer along at least said target sequence to produce an extended first primer, said first primer being capable of hybridizing to, and being extended along, (1) said extended first primer or (2) an extended second oligonucleotide primer ("second primer") wherein said extended second primer results from the extension of a second primer capable of hybridizing to and extending along a polynucleotide that is complementary (complementary polynucleotide) to said target sequence, (c) dissociating said extended first primer from said target sequence, (d) hybridizing, to the 3'-end of said extended first primer, said first or said second primer, (e) extending said first or said second primer along said extended first primer, (f) dissociating said extended first primer or said extended second primer from said extended first primer, (g) hybridizing, to the 3'-end of said extended first or said extended second primer, said first primer, and (h) repeating steps (e)–(g) by repeated temperature cycling, wherein said primer comprises a modified nucleotide in the portion thereof that binds to said target polynucleotide and wherein an antibody for said modified nucleotide is included in said combination, said antibody being capable of binding to said modified nucleotide and preventing said primer from being extended along said target sequence and wherein said antibody is released irreversibly from said primer during said temperature cycling thereby permitting said primer to bind with and be extended along said target polynucleotide sequence.

19. A method according to claim 18 wherein said modified nucleotide is an unnatural nucleotide or comprises a group that is unnatural.

20. A method according to claim 18 wherein said target polynucleotide is DNA or RNA.

21. A method according to claim 18 wherein only said first primer is used and said target sequence contains at its 5'-end at least a 10-base sequence hybridizable with a sequence at the 3'-end of said target sequence to which said primer hybridizes.

22. A method according to claim 18 wherein said first and said second primers are different and said extended first primer is a template for said second primer and said extended second primer is a template for said first primer.

23. A method according to claim 18 wherein said modified nucleotide is at the 3'-end portion of said oligonucleotide primer.

24. A method for detecting a target sequence of a target polynucleotide ("target sequence"), said method comprising:

(a) amplifying said target sequence by a method comprising:
   (i) hybridizing to the 3'-end of said target sequence a first oligonucleotide primer ("first primer"),
   (ii) extending, in the presence of a polymerase and nucleotide triphosphates, said first primer along at least said target sequence to produce an extended first primer, said first primer being capable of hybridizing to, and being extended along, (1) said extended first primer or (2) an extended second oligonucleotide primer ("second primer") wherein said extended second primer results from the extension of a second primer capable of hybridizing to and extending along a polynucleotide that is complementary (complementary polynucleotide) to said target sequence,
   (iii) dissociating said extended first primer from said target sequence,
   (iv) hybridizing, to the 3'-end of said extended first primer, said first or said second primer,
   (v) extending said first or said second primer along said extended first primer,
   (vi) dissociating said extended first primer or said extended second primer from said extended first primer,
   (vii) hybridizing, to the 3'-end of said extended first or said extended second primer, said first primer, and
   (viii) repeating steps (v)–(vii), and (b) detecting said extended first primer and/or said extended second primer, wherein said primer comprises a modified nucleotide in the portion thereof that binds to said target polynucleotide and wherein an antibody for said modified nucleotide is included in said combination, said antibody being capable of binding to said modified nucleotide and preventing said primer from being extended along said target sequence and wherein said antibody is released irreversibly from said primer during said temperature cycling thereby permitting said primer to bind with and be extended along said target polynucleotide sequence.

25. The method of claim 24 wherein the repeating of steps (v)–(vii) is achieved by repeated temperature cycling.

26. The method of claim 24 wherein said target polynucleotide is DNA or RNA.

27. The method of claim 24 wherein only said first primer is used and said target sequence contains at its 5'-end at least a 10-base sequence hybridizable with a sequence at the 3'-end of said target sequence to which said first primer hybridizes.

28. The method of claim 24 wherein said first and said second primers are different and said extended first primer is a template for said second primer and said extended second primer is a template for said first primer.

* * * * *